(12) United States Patent
Miklus et al.

(10) Patent No.: US 12,005,083 B1
(45) Date of Patent: Jun. 11, 2024

(54) NUTRITIONAL COMPOSITIONS WITH MFGM AND CERTAIN HUMAN MILK OLIGOSACCHARIDES AND USES THEREOF

(71) Applicant: PBM Nutritionals, LLC, Allegan, MI (US)

(72) Inventors: Michael Bernard Miklus, Essex Junction, VT (US); Anja Monika Wittke, Munich (DE); Pedro Antonio Prieto, Columbus, OH (US); Cynthia M. Barber, Gordonsville, VA (US)

(73) Assignee: PBM Nutritionals, LLC, Allegan, MI (US)

( * ) Notice: Subject to any disclaimer, the term of this patent is extended or adjusted under 35 U.S.C. 154(b) by 585 days.

(21) Appl. No.: 16/910,849

(22) Filed: Jun. 24, 2020

Related U.S. Application Data

(60) Provisional application No. 62/865,879, filed on Jun. 24, 2019.

(51) Int. Cl.

| | | |
|---|---|---|
| A61K 31/661 | (2006.01) | |
| A23L 2/66 | (2006.01) | |
| A23L 33/00 | (2016.01) | |
| A23L 33/12 | (2016.01) | |
| A23L 33/125 | (2016.01) | |

(Continued)

(52) U.S. Cl.
CPC ............... *A61K 35/20* (2013.01); *A23L 2/66* (2013.01); *A23L 33/12* (2016.08); *A23L 33/125* (2016.08); *A23L 33/15* (2016.08); *A23L 33/19* (2016.08); *A23L 33/40* (2016.08); *A61K 9/0056* (2013.01); *A61K 9/0095* (2013.01); *A61K 31/202* (2013.01); *A61K 31/355* (2013.01);

(Continued)

(58) Field of Classification Search
CPC .................................................. A61K 31/661
See application file for complete search history.

(56) References Cited

U.S. PATENT DOCUMENTS

| | | |
|---|---|---|
| 7,090,879 B2 | 8/2006 | Albrecht et al. |
| 7,572,474 B2 | 8/2009 | Petschow et al. |

(Continued)

FOREIGN PATENT DOCUMENTS

| | | |
|---|---|---|
| CN | 108522655 A | 9/2018 |
| WO | 2016086157 A1 | 6/2016 |

(Continued)

OTHER PUBLICATIONS

Vandenplas et al., "Human milk oligosaccharides: 2'-fucosyllactose (2'-FL) and lacto-N-neotetraose (LNnT) in infant formula", Nutrients, 10:1-12, 2018.*

(Continued)

*Primary Examiner* — Rosanne Kosson
(74) *Attorney, Agent, or Firm* — Greenberg Traurig, LLP; Elana B. Araj

(57) ABSTRACT

A nutritional composition that includes a milk fat globule membrane component, at least one human milk oligosaccharide, and at least one additional component chosen from the group consisting of DHA, ARA, Vitamin E, Vitamin C, and sphingomyelin. The nutritional composition is in the form of a ready-to-drink composition, a food supplement, an extruded food bar, or a solid oral dosage form. The nutritional composition is typically administered or provided to adults, children, or infants through consumption.

8 Claims, 14 Drawing Sheets

(51) Int. Cl.
*A23L 33/15* (2016.01)
*A23L 33/19* (2016.01)
*A61K 9/00* (2006.01)
*A61K 31/202* (2006.01)
*A61K 31/355* (2006.01)
*A61K 31/375* (2006.01)
*A61K 35/20* (2006.01)

(52) U.S. Cl.
CPC .......... *A61K 31/375* (2013.01); *A61K 31/661* (2013.01); *A23V 2002/00* (2013.01)

(56) References Cited

U.S. PATENT DOCUMENTS

| | | | |
|---|---|---|---|
| 7,618,669 B2 | 11/2009 | Rangavajla et al. |
| 7,829,126 B2 | 11/2010 | Barrett-Reis et al. |
| 8,021,708 B2 | 9/2011 | Petschow et al. |
| 8,075,934 B2 | 12/2011 | Banavara et al. |
| 8,076,282 B2 | 12/2011 | Hageman |
| 8,114,441 B2 | 2/2012 | Boehm et al. |
| 8,119,142 B2 | 2/2012 | Zwijsen et al. |
| 8,221,809 B2 | 7/2012 | Subramanian et al. |
| 8,263,147 B2 | 9/2012 | Barrett-Reis et al. |
| 8,277,863 B2 | 10/2012 | Petschow et al. |
| 8,287,931 B2 | 10/2012 | Rosales et al. |
| 8,287,932 B2 | 10/2012 | Rosales et al. |
| 8,293,264 B2 | 10/2012 | Rosales et al. |
| 8,425,955 B2 | 4/2013 | Wittke |
| 8,497,238 B2 | 7/2013 | Hageman et al. |
| 8,525,660 B2 | 9/2013 | Miller et al. |
| 8,535,659 B1 | 9/2013 | Morrison et al. |
| 8,546,325 B2 | 10/2013 | Hageman |
| 8,557,320 B2 | 10/2013 | Petschow et al. |
| 8,618,047 B2 | 12/2013 | Hofman et al. |
| 8,703,737 B2 | 4/2014 | Buck et al. |
| 8,871,218 B2 | 10/2014 | Zwijsen et al. |
| 9,089,157 B2 | 7/2015 | Wittke et al. |
| 9,414,618 B2 | 4/2016 | Shao et al. |
| 9,386,794 B2 | 7/2016 | Rosales et al. |
| 9,439,448 B2 | 9/2016 | Rosales et al. |
| 9,463,176 B2 | 10/2016 | Hageman |
| 9,539,269 B2 | 1/2017 | Chow et al. |
| 9,591,872 B2 | 3/2017 | Rosado Loria et al. |
| 9,757,345 B2 | 9/2017 | Walton et al. |
| 9,795,623 B2 | 10/2017 | Davis et al. |
| 9,808,474 B2 | 11/2017 | Buck et al. |
| 9,844,532 B2 | 12/2017 | Lai et al. |
| 9,861,120 B2 | 1/2018 | Barrett-Reis et al. |
| 10,039,765 B1 | 8/2018 | Toothman |
| 10,039,805 B1 | 8/2018 | Toothman |
| 10,328,049 B2 | 6/2019 | Lai et al. |
| 10,328,091 B2 | 6/2019 | De Castro et al. |
| 10,342,244 B2 | 7/2019 | Barrett-Reis et al. |
| 10,369,164 B2 | 8/2019 | Buck et al. |
| 10,471,081 B2 | 11/2019 | Chow et al. |
| 10,525,016 B2 | 1/2020 | Kuang et al. |
| 10,617,700 B1 | 4/2020 | Toothman |
| 10,624,916 B2 | 4/2020 | Duska-Mcewen et al. |
| 10,639,319 B2 | 5/2020 | Davis et al. |
| 10,709,721 B2 | 7/2020 | Sprenger et al. |
| 10,779,550 B2 | 9/2020 | Chow et al. |
| 10,806,169 B2 | 10/2020 | Laver et al. |
| 10,813,940 B2 | 10/2020 | Buck et al. |
| 10,973,837 B2 | 4/2021 | Buck et al. |
| 11,026,444 B2 | 6/2021 | Yan et al. |
| 11,122,833 B1 | 9/2021 | Toothman |
| 11,160,817 B2 | 11/2021 | Chow et al. |
| 11,179,406 B2 | 11/2021 | Chow et al. |
| 11,197,875 B2 | 12/2021 | Buck et al. |
| 11,260,088 B2 | 3/2022 | Barranco et al. |
| 11,278,047 B2 | 3/2022 | Destaillats |
| 11,311,562 B2 | 4/2022 | Davis et al. |
| 11,318,150 B1 | 5/2022 | Toothman |
| 11,337,990 B2 | 5/2022 | Buck et al. |
| 11,464,793 B2 | 10/2022 | Buck et al. |
| 11,524,018 B2 | 12/2022 | Buck et al. |
| 11,547,744 B2 | 1/2023 | McGrath et al. |
| 2007/0098849 A1 | 5/2007 | Barrett-Reis et al. |
| 2008/0003330 A1 | 1/2008 | Rueda et al. |
| 2014/0249103 A1 | 9/2014 | Buck et al. |
| 2016/0331017 A1 | 11/2016 | De Castro et al. |
| 2018/0104267 A1 | 4/2018 | Buck et al. |
| 2018/0161352 A1 | 6/2018 | Buck et al. |
| 2018/0161353 A1 | 6/2018 | Buck et al. |
| 2019/0247469 A1 | 8/2019 | McGrath et al. |
| 2020/0093846 A1 | 3/2020 | Chow et al. |
| 2020/0093847 A1 | 3/2020 | Buck et al. |
| 2020/0230162 A1 | 7/2020 | Duska-Mcewen et al. |
| 2020/0305488 A1 | 10/2020 | Binia et al. |
| 2021/0038620 A1 | 2/2021 | Buck et al. |
| 2021/0045423 A1 | 2/2021 | Laver et al. |
| 2021/0077512 A1 | 3/2021 | Buck et al. |
| 2021/0106038 A1 | 4/2021 | Wooster et al. |
| 2021/0228603 A1 | 7/2021 | Buck et al. |
| 2021/0315852 A1 | 10/2021 | Do et al. |
| 2021/0386107 A1 | 12/2021 | McGrath, Jr. et al. |
| 2021/0401021 A1 | 12/2021 | Laver et al. |
| 2022/0000892 A1 | 1/2022 | Garcia-Rodenas et al. |
| 2022/0022515 A1 | 1/2022 | Van Riet |
| 2022/0062311 A1 | 3/2022 | Garcia-Rodenas et al. |
| 2022/0079963 A1 | 3/2022 | Garcia-Rodenas et al. |
| 2022/0110357 A1 | 4/2022 | Chichlowski et al. |
| 2022/0226382 A1 | 7/2022 | Wada et al. |
| 2022/0249527 A1 | 8/2022 | Davis et al. |
| 2022/0354876 A1 | 11/2022 | Buck et al. |
| 2023/0013644 A1 | 1/2023 | Chichlowski et al. |

FOREIGN PATENT DOCUMENTS

| | | | | |
|---|---|---|---|---|
| WO | WO-2016086157 A1 | * | 6/2016 | ............... A23C 9/20 |
| WO | 2021197492 A1 | | 10/2021 | |
| WO | 2021231981 A1 | | 11/2021 | |
| WO | 2021257543 A1 | | 12/2021 | |
| WO | 2022078859 A1 | | 4/2022 | |
| WO | 2022101222 A1 | | 5/2022 | |
| WO | 2022117829 A1 | | 6/2022 | |
| WO | 2022182814 A1 | | 9/2022 | |
| WO | 2022190120 A1 | | 9/2022 | |
| WO | 2022190121 A1 | | 9/2022 | |
| WO | 2022226311 A1 | | 10/2022 | |
| WO | 2022266058 | | 12/2022 | |

OTHER PUBLICATIONS

Berenbaum, "Synergy, additivism and antagonism in immunosuppression, a critical review," Clin Exp Iummunol 28:1-18, 1977.*
English machine translation of Pang et al., CN 108522655 A, 2018.*
Bezelgues, J.B., Short Communication: Milk Fat Globule Membrane as a Potential Delivery System for Liposoluble Nutrients, Journal of Dairy Science, vol. 92, No. 6, 92:2524-2528 doi:10.3168/jds.2008-1725; American Dairy Science Association, 2009.
Pascual, Pet Anthony L., Effects of Different Types of Milk Fat Globule Membrane Materials on the Physical and Rheological Characteristics of Set Yoghurts, International Journal of Agriculture Innovations and Research (IJAIR), vol. 5, Issue 6, ISSN (online) 2319-1473, pp. 968-973.
Andreas, N. J., Kampmann, B., & Le-Doare, K. M. (2015). Human breast milk: A review on its composition and bioactivity. Early human development, 91 (11 ), 629-635. (Year: 2015).
Brenna, J. T., Varamini, B., Jensen, R. G., Diersen-Schade, D. A., Boettcher, J. A., & Arterburn, L. M. (2007). Docosahexaenoic and arachidonic acid concentrations in human breast milk worldwide. The American journal of clinical nutrition, 85(6), 1457-1464. (Year: 2007).
Brink, L. R., Gueniot, J. P., & Lonnerdal, B. (2019). Effects of milk fat globule membrane and its various components on neurologic development in a postnatal growth restriction rat model. The Journal of Nutritional Biochemistry, 69, 163-171. (Year: 2019).
Dewettinck, K., Rombaut, R., Thienpont, N., Le, T. T., Messens, K., & Van Camp, J. (2008). Nutritional and technological aspects of milk fat globule membrane material. International dairy journal, 18(5), 436-457. (Year: 2008).

(56) References Cited

OTHER PUBLICATIONS

Mills, S., Ross, R. P., Hill, C., Fitzgerald, G. F., & Stanton, C. (2011). Milk intelligence: Mining milk for bioactive substances associated with human health. International dairy journal, 21 (6), 377-401. (Year: 2011).

Timby, N., Domellof, M., Lonnerdal, B., & Hernell, O. (2015). Comment on Safety and tolerance evaluation of milk fat globule membrane-enriched infant formulas. Clinical Medicine Insights: Pediatrics, 9, CMPed-S27185. (Year: 2015).

* cited by examiner

NUTRITIONAL COMPOSITIONS WITH MFGM AND CERTAIN HUMAN MILK OLIGOSACCHARIDES AND USES THEREOF

CROSS-REFERENCE TO RELATED APPLICATIONS

This application claims priority under 35 U.S.C. § 119(e) to U.S. Provisional Application No. 62/865,879, filed Jun. 24, 2019, which is incorporated herein by reference in its entirety.

TECHNICAL FIELD

The present disclosure relates to nutritional compositions that include a milk fat globule membrane component, at least one human milk oligosaccharide, and at least one additional component chosen from the group consisting of: DHA, ARA, Vitamin E, Vitamin C, and sphingomyelin. The nutritional composition can be in the form of a ready-to-drink composition, a food supplement, an extruded food bar, or a solid oral dosage form. The present disclosure also relates to methods of using these nutritional compositions to improve health in adults, children, or infants.

BACKGROUND

Nutritional compositions are typically formulated and designed to provide the best possible nutrition in the most bioavailable form to the human body. Often formulations have relied on different forms of the various ingredients of nutritional compositions to provide better uptake or effects on the human body when the nutritional compositions are administered. Typically, the use of these more exotic ingredients are expensive component ingredients when used in various nutritional compositions to provide what sometimes is a marginal improvement over more standard ingredients. It would be preferred to find unexpectedly synergistic and unique combinations of ingredients that might facilitate the bioavailability and thereby increasing or promoting the development and health of humans of any age as well as lowering the risk of developing other health related conditions.

SUMMARY

An aspect of the present disclosure is generally directed toward a nutritional composition comprising: a milk fat globule membrane component, at least one human milk oligosaccharide and at least one additional component chosen from the group consisting of DHA, ARA, Vitamin E, Vitamin C, and sphingomyelin. The nutritional composition can be in the form of a ready-to-drink composition, a food supplement, an extruded food bar, or a solid oral dosage form.

Embodiments of this aspect of the invention directed toward the nutritional composition may include one or more of the following optional features. In some embodiments, the at least one human milk oligosaccharide comprises 2'FL. In some embodiments, the milk fat globule membrane component has a protein content of at least about 60% by weight of the milk fat globule membrane component. In some embodiments, the milk fat globule membrane has a lactose content of not more than about 5% by weight of the milk fat globule membrane component. In some embodiments, the milk fat globule membrane has a lactose content of not more than about 3% by weight of the milk fat globule membrane component. In some embodiments, the milk fat globule membrane component has a protein content of at least about 75% by weight of the milk fat globule membrane component. In some embodiments, the at least one human milk oligosaccharide consists of 2'FL and is free of dietary butyrate. In some embodiments, the at least one human milk oligosaccharide comprises at least one human milk oligosaccharide chosen from the group consisting of fucosyllactose, 2'FL, 3FL, Lacto-N-fucopentaose I (LNFP I), LNFP II, LNFP III, LNFP V, and mixtures thereof. In some embodiments, the nutritional composition is a ready-to-drink composition and comprises alpha tocopherol(s) and DHA. In some embodiments, the composition provides synergistically enhanced amounts of the docosahexaenoic acid (DHA) in the phospholipid form to the brain due to the synergistic combination of the at least one human milk oligosaccharide, the milk fat globule membrane and the DHA. In some embodiments, the nutritional composition is a ready-to-drink composition and further comprises docosahexaenoic acid (DHA), protein, fat, carbohydrate, vitamin C and alpha tocopherol(s). In some embodiments, the nutritional composition is a ready-to-drink composition and the human milk oligosaccharide consists of 2'FL and the milk fat globule membrane component has a protein content of at least about 60% by weight of the milk fat globule membrane component and lactose in an amount of not more than 10% by weight of the milk fat globule membrane component. In some embodiments, the nutritional composition is a compressed solid oral dosage form.

Another aspect of the present disclosure is generally directed to a method for supporting cognitive function and/or neuron cellular health. The method includes the step of administering a nutritional composition to an individual wherein the nutritional composition comprises a milk fat globule membrane component, at least one human milk oligosaccharide, and DHA where the milk fat globule membrane component and the at least one human milk oligosaccharide synergistically work together with the DHA to increase the level of a phospholipid form of DHA in the blood of the individual.

Embodiments of this aspect of the invention directed to the method for supporting cognitive function and/or neuron cellular health may include one or more of the following optional features. In some embodiments, the phospholipid form of DHA is a complex of DHA or ARA and another fatty acid chosen from the group consisting of palmitic acid, linoleic acid and stearic acid. In some embodiments, the at least one human milk oligosaccharide comprises 2'FL and the nutritional composition is an adult nutritional composition where the nutritional composition further comprises at least one additional component chosen from the group consisting of: ARA, Vitamin E, Vitamin C, and sphingomyelin. In some embodiments, the milk fat globule membrane component has a protein content of at least about 60% by weight of the milk fat globule membrane component. In some embodiments, the milk fat globule membrane has a lactose content of not more than about 5% by weight of the milk fat globule membrane component. In some embodiments, the milk fat globule membrane has a lactose content of not more than about 3% by weight of the milk fat globule membrane component. In some embodiments, the milk fat globule membrane component has a protein content of at least about 75% by weight of the milk fat globule membrane component. In some embodiments, the at least one human milk oligosaccharide consists of 2'FL and is free of any dietary butyrate. In some embodiments, the at least one human milk oligosaccharide comprises at least one human milk oligosaccharide chosen from the group consisting of fucosyllactose, 2'FL, 3FL, Lacto-N-fucopentaose I (LNFP I), LNFP II, LNFP III, LNFP V, and mixtures thereof. In some embodiments, the at least one human milk oligosaccharide is 2'FL and the milk fat globule membrane component comprises from about 10% to about 25% fat by weight of the milk fat globule component; water present in an amount such that the milk fat globule component has a moisture content of not more than 7% by weight of the milk fat globule component; ash present in an amount of not more than 5% by weight of the milk fat globule component; and one or more phospholipid where the total amount of phospholipids in the milk fat globule component is from about 4% to about 9% by weight of the milk fat globule component. In some embodiments, the nutritional composition is not derived from human breast milk and is not an infant formula composition or a human milk fortifier. In some embodiments, the composition provides synergistically enhanced amounts of the docosahexaenoic acid (DHA) in the phospholipid form due to the synergistic combination of the at least one human milk oligosaccharide, the milk fat globule membrane and the DHA. In some embodiments, the nutritional composition is free of butyrate.

Another aspect of the present disclosure is directed to the method of supporting brain health by increasing the transport of docosahexaenoic acid (DHA) at the blood brain barrier where the method includes the step of administering a nutritional composition configured for enteral administration to an individual over 2 years old and where the nutritional composition comprises a milk fat globule membrane component, at least one human milk oligosaccharide, DHA, and at least one additional component chosen from the group consisting of ARA, Vitamin E, Vitamin C, and sphingomyelin whereby the milk fat globule membrane component and the at least one human milk oligosaccharide synergistically work together with the DHA to increase the level of a phospholipid form of DHA that increases brain DHA levels.

Yet another aspect of the present disclosure is generally directed to a composition that comprises: one or a plurality of protein components such that the total amount of protein is from about 12 g to about 19 g in the composition; one or more carbohydrate components such that the total amount of carbohydrates is from about 60 g to about 85 g in the composition; one or more human milk oligosaccharides present in the composition in an amount of from about 0.2 g to about 3.0 g in the composition; phospholipids in an amount of from about 300 mg to about 800 mg in the composition; phosphatidylcholine in and amount of from about 10 mg to about 300 mg in the composition; sphingomyelin in an amount of from about 20 mg to about 400 mg in the composition; one or a plurality of fat components such that the total amount of fat in the composition is from about 25 g to about 45 g; arachidonic acid in an amount of from about 75 mg to about 275 mg in the composition; docosahexaenoic acid in an amount of from about 37 mg to about 180 mg in the composition; and linoleic acid in and amount of from about 4500 mg to about 9500 mg in the composition. The composition can be an adult nutritional for enteral administration to a human adult.

Embodiments of this aspect of the invention directed to the composition may include one or more of the following optional features. In some embodiments, the composition is free of butyrate at the time of administration. In some embodiments, the composition comprises a milk fat globule component derived from whey protein concentrate. In some embodiments, the milk fat globule component has a protein content of at least about 60% by weight of the milk fat globule component. In some embodiments, the milk fat globule component has a protein content of at least about 70% by weight of the milk fat globule component. In some embodiments, the milk fat globule component has a protein content of from about 60% to about 80% by weight of the milk fat globule component. In some embodiments, the milk fat globule component has a lactose content of not more than about 10% by weight of the milk fat globule component. In some embodiments, the milk fat globule component comprises from about 10% to about 25% fat by weight of the milk fat globule component; water, wherein the water is present in an amount such that the milk fat globule component has a moisture content of not more than 7% by weight of the milk fat globule component; ash present in an amount of not more than 5% by weight of the milk fat globule component; and one or more phospholipid where the total amount of phospholipids in the milk fat globule component is from about 4% to about 9% by weight of the milk fat globule component. In some embodiments, the milk fat globule component further comprises water, where the water is present in an amount such that the milk fat globule component has a moisture content of not more than 7% by weight of the milk fat globule component. In some embodiments, the one or more human milk oligosaccharide is chosen from the group consisting of 2'FL, 3FL, Lacto-N-fucopentaose I (LNFP I), LNFP II, LNFP III, LNFP V, and mixtures thereof. In some embodiments, the at least one human milk oligosaccharide consists of 2'FL. In some embodiments, the composition may further comprise at least one additional component chosen from the group consisting of: ARA, Vitamin E, and Vitamin C. In some embodiments, the composition may further comprise a plurality of additional components chosen from the group consisting of: ARA, Vitamin E, and Vitamin C. In some embodiments, the composition is a solid oral dosage form, a capsule, a ready-to-drink composition or a suspension and no ingredient of the composition is derived from human breast milk.

Another aspect of the present disclosure is generally directed to a method of reducing the risk of losing visual acuity by increasing bioavailability of alpha tocopherol(s) that includes the step of administering a composition to a human over the age of two a dosage form of the composition that is not an infant formula or a human milk fortifier. The composition according to this aspect of the present disclosure includes: a milk fat globule membrane component, at least one human milk oligosaccharide, at least one alpha tocopherol in the form of a racemic blend of alpha tocopherols or RRR alpha tocopherol and at least one additional component chosen from: DHA, ARA, Vitamin C, and sphingomyelin and where the milk fat globule membrane component and the at least one human milk oligosaccharide synergistically work together with the at least one alpha tocopherol to increase the level of alpha tocopherols in the blood plasma of the human.

Another aspect of the present disclosure is generally directed to a method of supporting visual health by increasing bioavailability of alpha tocopherol(s) where the method includes the step of administering an adult nutritional composition comprising: a milk fat globule membrane component, at least one human milk oligosaccharide, and at least one alpha tocopherol.

Embodiments of this aspect of the invention directed to the method of supporting visual health by increasing bioavailability of alpha tocopherol(s) may include one or more of the following optional features. In some embodiments, the at least one human milk oligosaccharide comprises 2'FL and the adult nutritional composition optionally further comprises lutein. In some embodiments, the milk fat globule membrane component has a protein content of at least about 60% by weight of the milk fat globule membrane component. In some embodiments, the milk fat globule membrane has a lactose content of not more than about 5% by weight of the milk fat globule membrane component. In some embodiments, the milk fat globule membrane has a lactose content of not more than about 3% by weight of the milk fat globule membrane component. In some embodiments, the milk fat globule membrane component has a protein content of at least about 75% by weight of the milk fat globule membrane component. In some embodiments, the at least one human milk oligosaccharide consists of 2'FL. In some embodiments, the at least one human milk oligosaccharide comprises at least one human milk oligosaccharide chosen from the group consisting of fucosyllactose, 2'FL, 3FL, Lacto N fucopentaose I (LNFP I), LNFP II, LNFP III, LNFP V, and mixtures thereof. In some embodiments, the adult nutritional composition is a tablet, capsule, caplet, suspension, food bar, or a ready-to-drink composition. In some embodiments, the nutritional composition does not include any component derived from human breast milk. In some embodiments, the composition provides synergistically enhanced amounts of the at least one alpha tocopherol due to the synergistic combination of the at least one human milk oligosaccharide, the milk fat globule membrane and the at least one alpha tocopherol. In some embodiments, the adult nutritional composition further comprises docosahexaenoic acid (DHA). In some embodiments, the adult nutritional composition is a compressed solid oral dosage form.

Yet another aspect of the present disclosure is generally directed to a method of supporting mental health where the method includes the step of administering an adult nutritional composition to a human over the age or 13. The adult nutritional composition has a milk fat globule membrane component, at least one human milk oligosaccharide, DHA, and at least one additional component chosen from the group consisting of ARA, Vitamin E, Vitamin C, and sphingomyelin. The milk fat globule membrane component and the at least one human milk oligosaccharide synergistically work together with the DHA to increase the level of a phospholipid form of DHA that increases brain DHA levels.

Embodiments of this aspect of the invention directed to the method of supporting mental health may include one or more of the following optional features. In some embodiments, the at least one human milk oligosaccharide comprises 2'FL. In some embodiments, the milk fat globule membrane component has a protein content of at least about 60% by weight of the milk fat globule membrane component. In some embodiments, the milk fat globule membrane has a lactose content of not more than about 5% by weight of the milk fat globule membrane component. In some embodiments, the milk fat globule membrane has a lactose content of not more than about 3% by weight of the milk fat globule membrane component. In some embodiments, the milk fat globule membrane component has a protein content of at least about 75% by weight of the milk fat globule membrane component. In some embodiments, the at least one human milk oligosaccharide consists of 2'FL. In some embodiments, the at least one human milk oligosaccharide comprises at least one human milk oligosaccharide chosen from the group consisting of: fucosyllactose, 2'FL, 3FL, Lacto-N-fucopentaose I (LNFP I), LNFP II, LNFP III, LNFP V, and mixtures thereof. In some embodiments, the adult nutritional composition is free of dietary butyrate. In some embodiments, the adult nutritional composition does not include any ingredient derived from human breast milk. In some embodiments, the adult nutrition composition provides synergistically enhanced amounts of the docosahexaenoic acid (DHA) in the phospholipid form due to the synergistic combination of the at least one human milk oligosaccharide, the milk fat globule membrane and the DHA. In some embodiments, the adult nutritional composition further comprises Vitamin C; at least one alpha tocopherol and fat, protein, and carbohydrates such that the adult nutritional composition provides complete human nutrition for a meal. In some embodiments, the nutritional composition is a solid oral dosage form, a human masticatable food product or a ready-to-drink beverage composition. In some embodiments, the adult nutritional composition is free of dietary butyrate.

These and other aspects, objects, and features of the present invention will be understood and appreciated by those skilled in the art upon studying the following specification, claims, and appended drawings. Any of the aspects, embodiments, or features of the present inventions disclosed herein may be combined with any or all of the aspects, embodiments, or features of any of the inventions described in the present disclosure generally.

BRIEF DESCRIPTION OF THE DRAWINGS

The following figures are provided by way of example and are not intended to limit the scope of the claimed invention.

DETAILED DESCRIPTION

Figure 1:
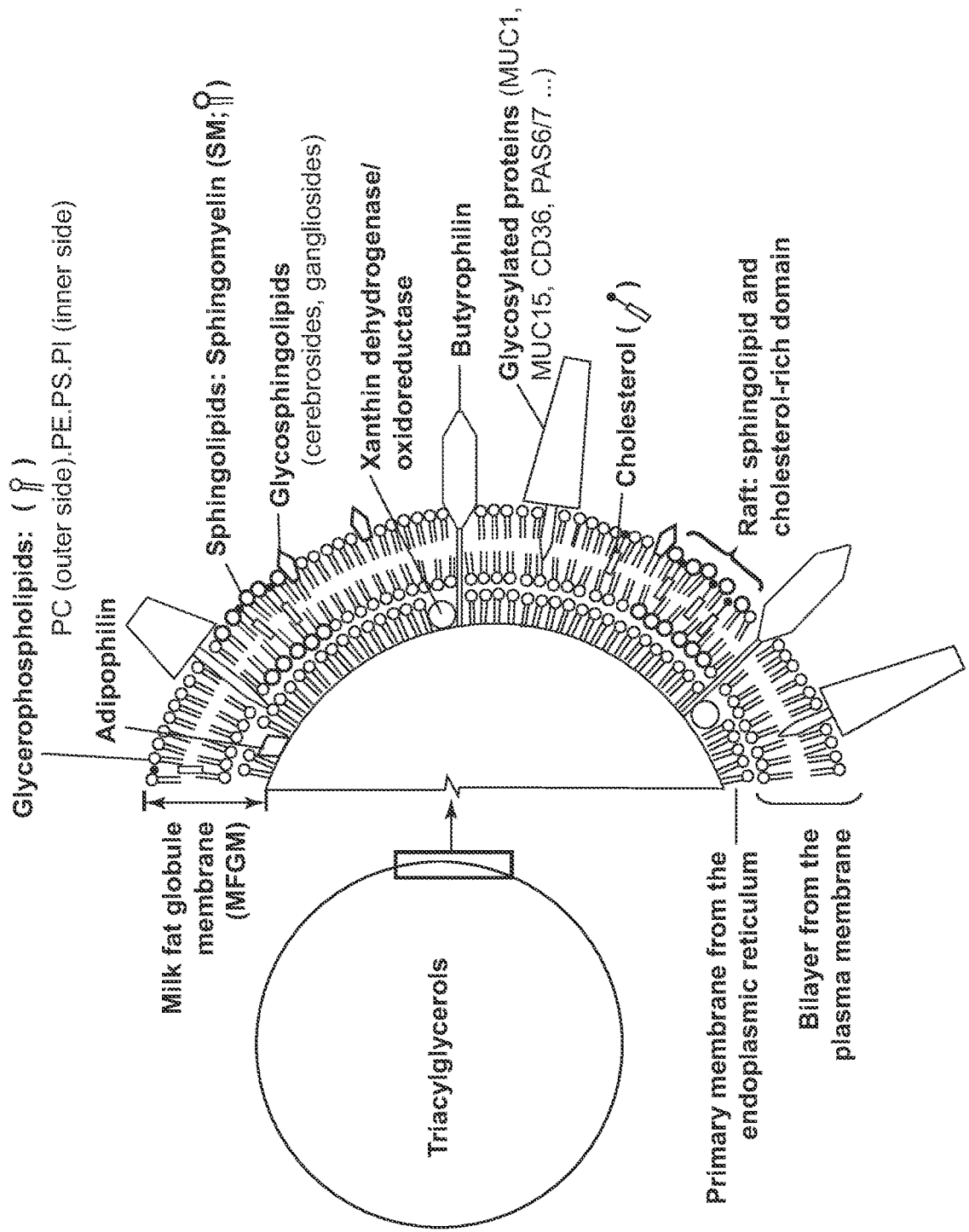
FIG. 1 is a schematic representation of the structure of the milk fat globule membrane.

It is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, 10) contained within the range. In this specification and the appended claims, the singular forms "a," "an" and "the" include plural reference unless the context clearly dictates otherwise. All combinations of method or process steps as used herein can be performed in any order, unless otherwise specified or clearly implied to the contrary by the context in which the referenced combination is made.

The various embodiments of the nutritional compositions and infant formulas of the present disclosure may also be substantially free of any ingredient or feature described herein, provided that the remaining formula still contains all of the required ingredients or features as described herein. In this context, and unless otherwise specified, the term "substantially free" means that the selected composition contains less than a functional amount of the optional ingredient, typically less than 1%, including less than 0.5%, including less than 0.1%, and also including zero percent, by weight of such optional or selected essential ingredient.

The nutritional compositions of the present disclosure described herein, including but not limited to compositions infant formulas, solid oral dosage forms, powders, and ready-to-drink compositions, and corresponding manufacturing methods may comprise, consist of, or consist essentially of the elements of the products as described herein, as well as any additional or optional element described herein or otherwise useful in nutritional product applications. "Consisting essentially of" in the context of the claims of this application limits the scope of a claim or claim element to the specified materials or steps "and those that do not materially affect the basic and novel characteristic(s)" of the claimed invention as would be known by those of ordinary skill in the art whether or not such a composition is disclosed in the application or not as affecting the basic and novel characteristic.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When it is intended to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

"Infant formula" is a composition that provides at least a portion, but more typically substantially all or all of the nutrient requirements of an infant. In the United States, the content of an infant formula is dictated by the federal regulations set forth in 21 C.F.R. Sections 100, 106 and 107. The term "infant formula" as used herein, unless otherwise specified, refers to liquid and solid nutritional products suitable for consumption by an infant as a main source of nutrition. The term "infant formula" does not include human breast milk and instead is produced artificially by humans. The "infant formula(s)" of the present disclosure may be generally referred to or included by the more general term "nutritional composition(s)".

An "infant" is a human ranging from 0 to 12 months corrected age, which means an infant's chronological age minus the amount of time that the infant was born premature (before the 37$^{th}$ week of gestation). An infant's "corrected age" is the age at which it would have been if it had been born at full term.

The nutritional composition(s) referenced in this application may be in the form of liquids, powders, gels, pastes, solids, concentrates, suspensions, or ready-to-use forms of enteral formulas, oral formulas, formulas for infants, formulas for pediatric subjects, formulas for children, growing-up milks, fortifiers, and/or formulas for adults, which are typically in the form of ready-to-drink products/formulas, powders or a solid oral dosage form such as a tablet, capsule, pill, caplet, or ready-to-mix powder. The nutritional composition may also include a compressed formula tablet that dissolves in water to be reconstituted into the ready to consume composition.

A "child" is typically a human ranging from about 12 months old to about 13 years old, but can refer to someone at any age or range of ages therebetween.

As used herein, all concentrations expressed as either "µg/liter" or "mg/liter" refer to ingredient concentrations within the described infant formulas as calculated on an as-fed basis, unless otherwise specified.

The nutritional compositions of the present disclosure typically contain enough levels of carbohydrates, fats and protein to provide nutritionally complete amounts of these components to the subject. "Nutritionally complete" is that the composition is able to provide qualitatively and quantitatively adequate amounts of all carbohydrates, lipids, essential fatty acids, proteins, essential amino acids, conditionally essential amino acids, vitamins, minerals and energy required for growth of the subject being provided with the nutritional composition at a given age. Typically, infant formulas of the present disclosure will have protein in an amount of from about 12 g to about 19 g per reconstituted liter (RL), carbohydrate in an amount of from about 60 g to about 85 g per reconstitute liter (RL), and fat in an amount of from about 25 g to about 45 g per reconstituted liter (RL). The amounts of various components will be adjusted to be "nutritionally complete" depending on the age of the subject, including whether that is an infant which is preterm (younger than 37 weeks) or one that is at least term.

Generally speaking, the present disclosure is directed to the surprising and unexpected effect of the co-administration of milk fat globule membrane (MFGM) with one or more human milk oligosaccharides including, for example, 2'FL ("2FL"). Additionally, due to their structural similarly, it is believed that the following human milk oligosaccharide would demonstrate the same effect: fucosyllactose, 3FL, 2'FL, Lacto-N-fucopentaose I (LNFP I), LNFP II, LNFP III, LNFP V, or mixtures thereof. The co-administration of MFGM and one or more of these specific HMOs surprisingly and significantly increased the bioavailability of sphingomyelin, and alpha-tocopherol and DHA and ARA through their complexation with phosphatidylcholines.

Additionally, it has been discovered that the co-administration of MFGM, 2'FL and lactoferrin (LF) has surprising and unexpected beneficial effects on nicotinamide metabolites, ascorbate metabolite, and threonate metabolite, which were all significantly higher than in the control group.

Most supplements or formulas with DHA derived from fish oil, krill oil, or algae do not increase brain DHA. Fatty acids are hydrolyzed in the intestine and absorbed as triglycerides. However, transport of DHA at the blood brain barrier is specific for the phospholipid form of DHA. The dietary administration of a DHA form of lysophosphatidylcholine has shown to increased brain DHA levels. However, the nutritional compositions of the present disclosure do not require the administration of this particular DHA form (lysophosphatidylcholine) and facilitates an uptake of a currently used fish oil/algae/fungal DHA form when incorporated into nutritional compositions such as ready-to-drink systems, solid dosage forms and an infant formula when administered in combination with MFGM and 2'FL. The combination of MFGM, 2'FL and LCPUFAs, including DHA and ARA, when enterally administered surprisingly and unexpectedly increases blood levels of DHA-phospholipid significantly. An increased DHA form present in plasma suggests an increased uptake of this form into the brain and consequently beneficial health outcomes for an infant/premature infant, adult, diabetic individual/pregnant women, obese adult, adult with neurological disease and an aging adult.

The MFGM ingredient of the present disclosure is very low in DHA, therefore not providing any relevant amounts of DHA or ARA. However, dietary phospholipids from MFGM can obviously deliver fatty acids from the digestive tract into the plasma. In rodents, the administration of MFGM was able to change brain lipids. MFGM can change the gut microbiome and together with the oligosaccharide 2'FL creates an environment that promotes the uptake of fatty acids, sphingomyelin and alpha-tocopherol.

Docosahexaenoic Acid ("DHA")

DHA is a long-chain, highly unsaturated omega-3 fatty acid. In the human body DHA is found in the bloodstream, transported via lipoproteins (with triglycerides, phospholipids or cholesterol esters) and in several organs. The highest DHA concentrations are found in the brain and eye compared to other organs. The brain consists mostly of lipids which are structured lipids like phospholipids. DHA is found in all cell membranes esterified into phospholipids and other complex lipids, regulating intracellular signaling. Brain DHA is involved in neuronal signaling and in the eye in the quality of vision. A lower DHA content has been linked to poorer cognitive development and visual function, consequently an appropriate supply during early life is crucial to ensure optimal development. There is a linear relationship between the DHA contents of maternal and umbilical cord plasma phospholipids, suggesting that maternal plasma levels determines DHA supply to the fetus. "Docosahexaenoic acid" (DHA) is a primary structural component of the human brain, cerebral cortex, skin, and retina. In physiological literature, it is given the name 22:6(n-3). It can be synthesized from alpha-linolenic acid or obtained directly from maternal milk (breast milk), fish oil, or algae oil. DHA is a carboxylic acid (-oic acid) with a 22-carbon chain and six (hexa-) cis double bonds (-en-); with the first double bond located at the third carbon from the omega end. DHA is a major fatty acid in brain phospholipids and the retina.

DHA will typically be utilized in amounts of from about 37 mg to about 180 mg per reconstituted liter (RL) of nutritional composition, more typically from about 60 mg to about 115 mg per reconstituted liter.

Arachidonic Acid ("ARA" or "AA")

ARA is one of the most abundant fatty acids in the brain and a relative stable concentration of ARA in human milk has been found, suggesting the importance of ARA at a time when brain growth and development is crucial. Diets low in LCPUFA showed an adverse effect in a rodent model on the development of myelin lipids that are important in early brain development. When ARA-phosphatidylcholine was added to artificial formula, the uptake was significantly higher in the brain than ARA provided as ARA-triglyceride in neonatal baboons. ARA is not only important for brain development, it is also a precursor for eicosanoids which play an important role in immunity and inflammation. ARA is important in the hormonal regulation of normal bone formation by increasing insulin-like growth factor gene expression and induction of osteoblast-dependent bone formation.

ARA will typically be utilized in amounts of from about 75 mg to about 275 mg per reconstituted liter (RL) of nutritional composition, more typically from about 120 mg to about 230 mg per reconstituted liter. Linoleic acid may also be present and will typically be utilized in amounts of from about 4500 mg to about 9500 mg per reconstituted liter (RL) of nutritional composition.

"Milk Fat Globule Membrane" (MFGM)

MFGM is a complex and unique structure composed primarily of lipids and proteins that surrounds milk fat globule secreted from the milk producing cells of humans and other mammals. It is a source of multiple bioactive compounds, including phospholipids, glycolipids, glycoproteins, and carbohydrates that have important functional roles within the brain and gut.

MFGM is a structurally complex bioactive milk component, found in human milk as well as the milk of other mammalian species. The MFGM in human milk contains many bioactive components with diverse functions and has been linked to cognitive and health benefits to infants. Some compositional differences are reported to exist between species, but bovine MFGM, the best-studied non-human source, generally contains a lipid and protein composition, which is similar to that of human MFGM.

MFGM makes up an estimated 2-6% of the total fat globules. Raw milk has an average total fat content around 4%. As a result, it contains around 0.08-0.24% MFGM. The content of MFGM in dairy products varies depending on the processing involved.

For example, infant formulas traditionally were lacking the MFGM because this fraction is lost during regular dairy processing. However, more recent advances in technology have facilitated the separation of MFGM from the fat globule, allowing bovine MFGM to be added in concentrated form. The MFGM fraction is now commercially available and can be added to infant formula or other nutritional products.

While it is believed that any milk material typically used to produce MFGM will provide the synergistic effects, including skim milk powder (SMP), buttermilk powder (BMP) and butter serum powder (BSP), the MFGM source used in the present disclosure is quite unique and is derived from whey protein sources. One such whey protein source may be MFGM10-WPC from Arla Foods of Basking Ridge, NJ. As shown in the chart below (all amounts are percent by weight), the MFGM produced from whey protein sources has significantly higher protein content and significantly lower lactose content than the other forms of MFGM. It is possible that the unique characteristics of this MFGM produced from whey protein sources provide a basis for the synergistic uptakes when the combination of MFGM and 2'FL or the combination of MFGM, 2'FL and LF are administered with other active ingredients in the nutritional compositions of the present disclosure, especially infant formulas.

| MFGM Source Material | Protein | Fat | Polar lipids | Ash | Lactose |
|---|---|---|---|---|---|
| SMP | 33.75 | 1.85 | | 9.19 | 55.19 |
| BMP | 34.16 | 9.96 | 3.36 | 7.49 | 49.10 |

-continued

| MFGM Source Material | Protein | Fat | Polar lipids | Ash | Lactose |
|---|---|---|---|---|---|
| BSP | 30.77 | 13.60 | 9.33 | 8.05 | 47.57 |
| MFGM10-WPC | 75.78 | 18.94 | 7.00 | 3.15 | 2.10 |

The MFGM produced from whey protein sources may have a protein content of at least about 60% by weight, more typically at least about 70% by weight and a lactose content of about 5% by weight or less, more typically about 3.5% by weight or less and most typically about 2.1% or less. Most typically, the MFGM ingredient will have the following subcomponent ingredient amounts:

| Range in MFGM Ingredient from whey protein source | Percent by weight of the MFGM ingredient |
|---|---|
| Protein | 60%-80% |
| Fat | 10%-25% |
| Moisture | NMT 7% |
| Lactose | NMT 10% |
| Ash | NMT 5% |
| Phospholipids | 4%-9% |

MFGM has beneficial effects on brain structure and function, intestinal development, and immune defense. MFGM also has beneficial effects on cognitive function maintaining brain, immunity, and gut health. In populations ranging from premature infants to preschool-age children, dietary supplementation with MFGM or its components has been associated with improvements in cognition and behavior, gut and oral bacterial composition, fever incidence, and infectious outcomes including diarrhea and otitis media.

MFGM may also play a role in supporting cardiovascular health by modulating cholesterol and fat uptake. MFGM affects cardiovascular disease by lowering serum cholesterol and triacylglycerol levels as well as blood pressure.

As shown in FIG. 1, the MFGM structure is very complex. It typically includes phospholipids, glycolipids, proteins and glycoproteins as well as cholesterol and other lipids. MFGM includes gangliosides, sphingolipids and phospholipids, which are particularly beneficial for brain development and cognitive health and function. A "ganglioside" is a molecule composed of a glycosphingolipid (ceramide and oligosaccharide) with one or more sialic acids (e.g. n-acetylneuraminic acid, NANA) linked on the sugar chain. "Sphingolipids" are a class of lipids containing a backbone of sphingoid bases, a set of aliphatic amino alcohols that includes sphingosine. In some aspects, there will typically be from about 20 mg to about 400 mg of sphingomyelin in nutritional compositions produced according to the present disclosure. "Phospholipids" are a class of lipids. They can form lipid bilayers because of their amphiphilic characteristic. The phospholipid molecule typically contains two hydrophobic fatty acid "tails" and a hydrophilic "head" consisting of a phosphate group. The two components are joined by a glycerol molecule. The phosphate groups can be modified. In some aspects, the nutritional compositions according to the present disclosure will typically have from about 300 mg to about 800 mg phospholipids. The compositions my contain egg phospholipids or be substantially free or free of egg phospholipids. Other than the DHA and ARA, another particularly beneficial class of phospholipids that may be included in the compositions of the present disclosure are phosphatidylcholines (PC).

Other than these phospholipids do not appear to have the same synergistic interaction with the other components of the present disclosure.

During lactation the milk fat globule membrane is secreted from the mammary gland, combining phospholipids, several proteins and cholesterol while surrounding the triacylglycerol core. The MFGM ingredient is comprised of three layers of bioactive molecules, including lipids, cholesterol, proteins, and glycoproteins. The phospholipids are composed of sphingomyelin, phosphatidylcholine, phosphatidylethanolamine, phosphatidylserine and phosphatidylinositol. The MFGM glycosphingolipids include cerebrosides and gangliosides, both have been described as important ingredients in the development of the immune system in the gut. A variety of proteins are part of MFGM, like α-lactalbumin, lysozyme, (3-casein, lactoferrin and immunoglobulins, suggesting that they also contribute to immune response. Feeding an infant formula with MFGM resulted in cognitive scores similar to breast fed infants, which were significantly higher compared to non-supplemented infant.

Human Milk Oligosaccharides

Figure 2:
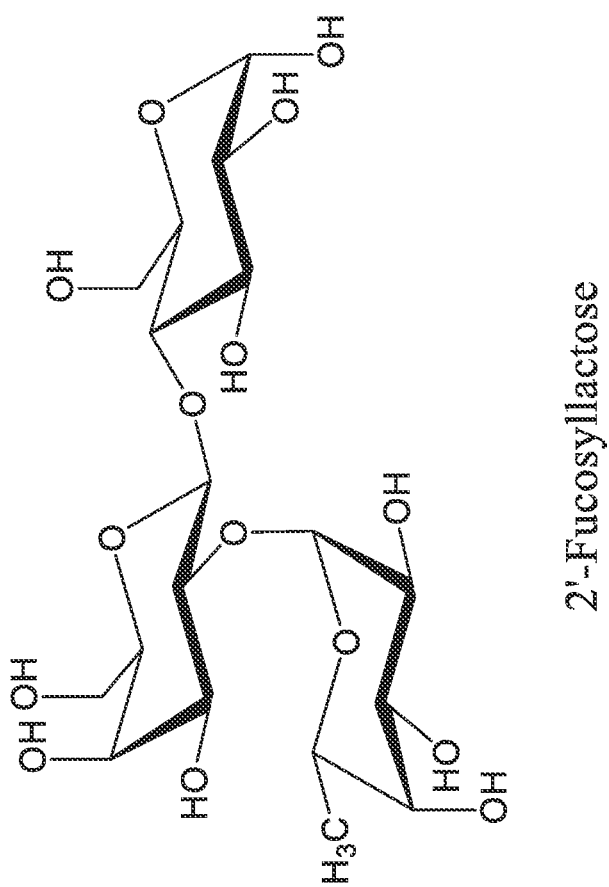
FIG. 2 is the chemical structure of 2'-fucosyllactose (2'FL).
Figure 3:
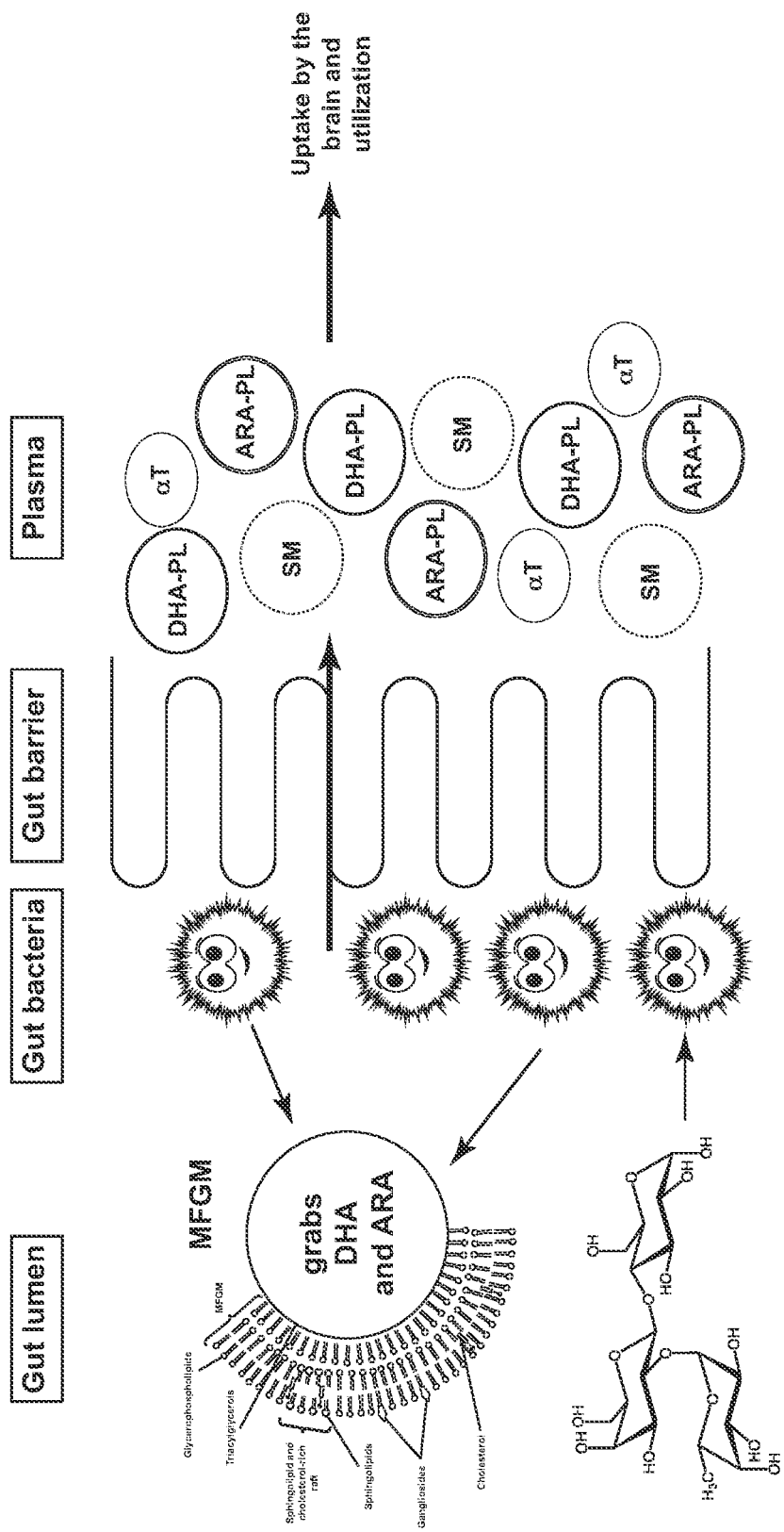
FIG. 3 is a simplified schematic representation of the mechanism of the present disclosure believed to increase the uptake of docosahexaenoic acid (DHA), arachidonic acid (ARA), sphingomyelin, and alpha tocopherol through the combined administration of MFGM and 2'FL in the gut lumen.

Human milk oligosaccharides are also used in the nutritional compositions of the present disclosure. Human milk oligosaccharides (HMOs) are a family of structurally diverse unconjugated glycans that are highly abundant in and unique to human milk. It has been surprisingly found that HMOs, in particular 2'-fucosyllactose (referred to herein as either "2'FL" or "2FL"), when administered with MFGM significantly enhances the absorption of other components of the nutritional compositions of the present disclosure across the intestinal wall and increase their absorption of these other components in the subject administered the nutritional compositions of the present disclosure. The chemical structure of 2'-fucosyllactose is provided in FIG. 2. Referring now to FIG. 3, a simplified schematic representation of the mechanism believed to take place in the current disclosure increases the uptake of docosahexaenoic acid (DHA), arachidonic acid (ARA), sphingomyelin, and alpha tocopherol through the combined administration of MFGM and 2'FL in the gut lumen. This occurs in individuals when administered nutritional compositions having the compositions of the present disclosure containing MFGM and 2'FL as discussed further below. The particular HMOs believed to provide the same or similar synergistic effects other than 2'FL include 3FL, Lacto-N-fucopentaose I (LNFP I), LNFP II, LNFP III, LNFP V, or mixtures thereof.

The nutritional compositions of the present disclosure may contain HMO, which in some aspects can include 2'FL, either alone or in combination with other HMOs, in an amount of from about 0.2 g to about 5.0 g, from about 0.2 g to about 4.0 g, from about 0.2 g to about 3.0 g, from about 0.2 g to about 2.0 g, or from about 0.2 g to about 1.0 g per reconstituted liter (RL).

Phosphatidylcholines

Newborn piglets were fed either a control diet (G1), a diet supplemented with MFGM (G3), or a diet supplemented with MFGM and 2'FL (G5) for 14 days. All of the fed diets were supplemented with DHA and ARA at the same level. These polyunsaturated fatty acids are important fatty acids for an individual or infant's growth and development. Blood samples were drawn on day 0 and day 14 and a metabolomic analysis determined difference in the plasma between the feeding groups.

Figure 5B:
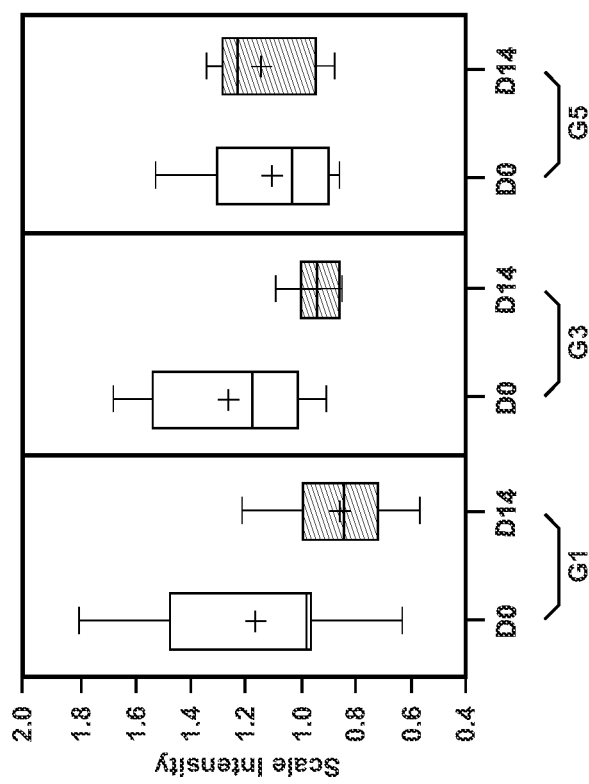
FIGS. 5A and 5B are box charts showing the plasma levels of phosphatidylcholines over time on day 0 and day 14 in piglets given: a control diet, the first column; a diet containing MFGM, the second column; and a formula/composition containing both the MFGM and 2'FL, the third column.
Figure 5A:
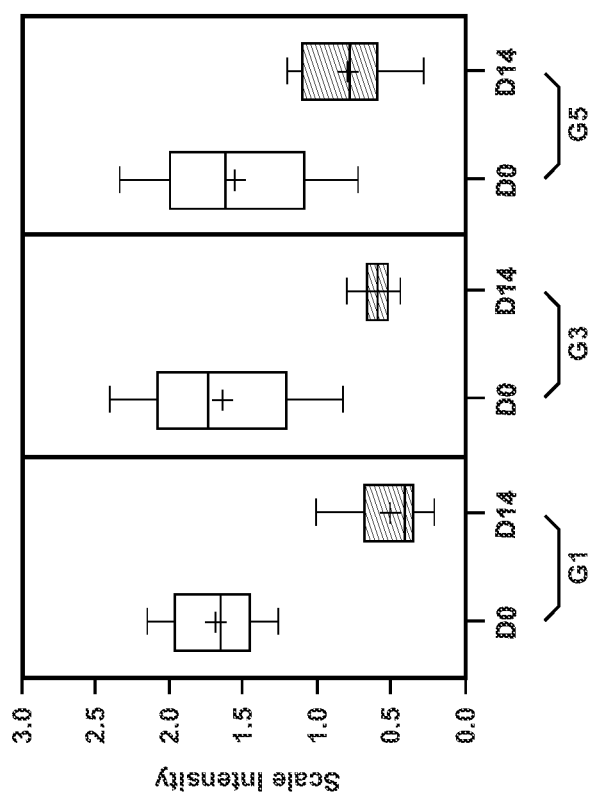

Referring to FIGS. 5A and 5B, the plasma levels of 1-linoleoyl-2-arachidonoyl-GPC (18:2/20:4n6) (see FIG. 5A) and 1-stearoyl-2-arachidonoyl-GPC (18:0/20:4) (see FIG. 5B) are illustrated in piglets fed the control (G1), MFGM supplemented (G3), or MFGM and 2'FL supplemented (G5) diets on day 0 and day 14. FIGS. 5A and 5B show the unexpected and surprisingly higher plasma levels of phosphatidylcholine containing the fatty acid arachidonic acid (20:4, ARA), namely 1-linoleoyl-2-arachidonoyl-GPC (18:2/20:4n6) and 1-stearoyl-2-arachidonoyl-GPC (18:0/20:4) in piglets who were fed compositions/nutritional compositions containing both MFGM and 2'FL, respectively. For most piglet groups the phosphatidylcholines decreased over time, from study start at day 0 to day 14.

The combination of MFGM and 2'FL modulated plasma metabolites in newborn piglets following 14 days of feeding. Several metabolites were changed to a greater extent in the MFGM+2'FL group than feeding MFGM alone. Phosphatidylcholines with DHA and ARA were higher in the plasma of piglets fed a diet with MFGM+2'FL compared to a control diet. Phosphatidylcholine (PC) is an important component of mammalian membranes that maintain membrane integrity and facilitate cell signaling. In addition, these fatty acids are important for membranes, inflammation, neurite growth, and brain development.

Considering the change from study day 0 to day 14 for plasma levels of 1-linoleoyl-2-arachidonoyl-GPC (18:2/20:4n6) as shown in FIG. 5A, the drop was significant in all feeding groups. Referring to FIG. 5B, the drop in the 1-stearoyl-2-arachidonoyl-GPC (18:0/20:4) plasma level was only significant for the control group (G1) and the MFMG fed piglet group (G3). In the group receiving MFGM+2'FL (G5), the level of the phosphatidylcholine did not decrease over time.

Figure 6A:
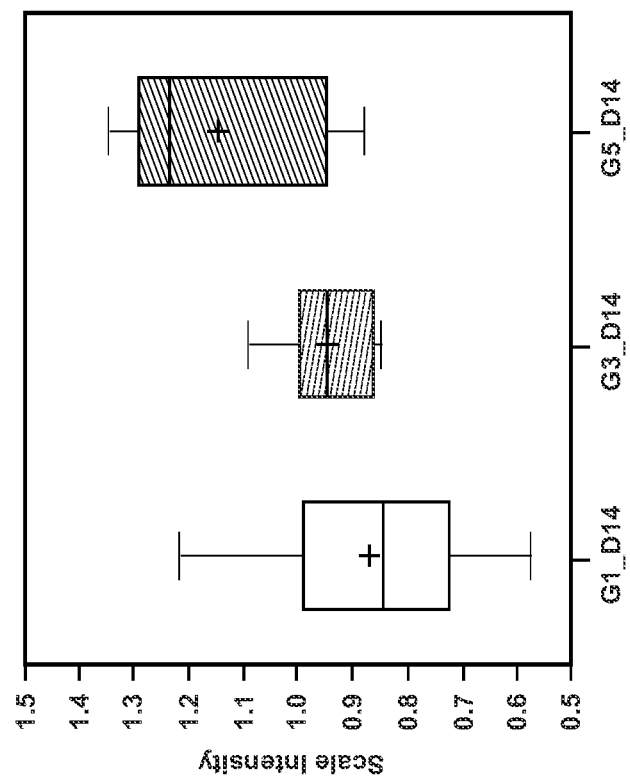
FIG. 6A shows the day 14 plasma concentration levels of FIG. 5A and shows the surprisingly higher plasma concentrations of phosphatidylcholines with ARA—1-linoleoyl-2-arachidonoyl-GPC (18:2/20:4n6).
Figure 6B:
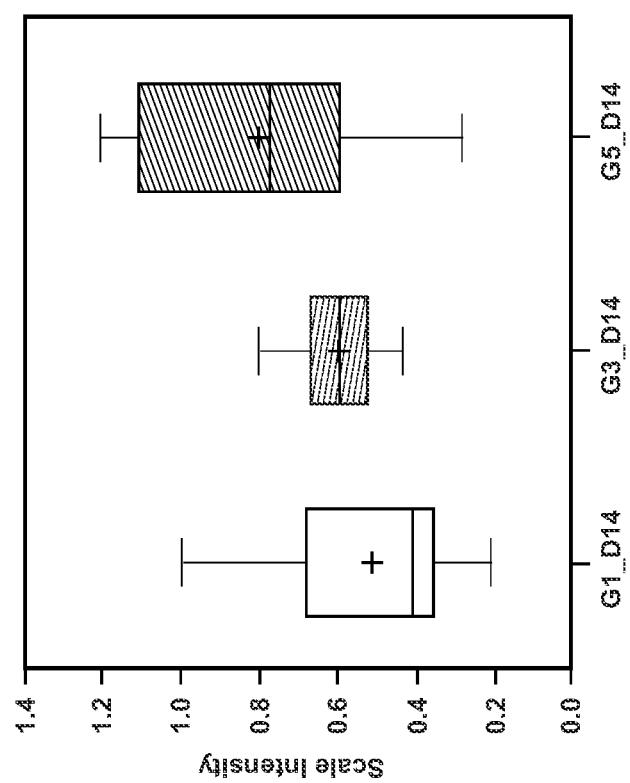
FIG. 6B shows the day 14 plasma concentration levels of FIG. 5B and shows the surprisingly higher plasma concentrations of phosphatidylcholines with ARA—1-stearoyl-2-arachidonoyl-GPC (18:0/20:4).

Referring now to FIGS. 6A and 6B, the plasma levels of 1-linoleoyl-2-arachidonoyl-GPC (18:2/20:4n6) and 1-stearoyl-2-arachidonoyl-GPC (18:0/20:4) in piglets on day 14 are illustrated. By comparing the phosphatidylcholine containing arachidonoyl (20:4) plasma levels on day 14 between the various diets, it can be noted that the MFGM supplemented diet group (G3) did not change the arachidonoyl (20:4) plasma levels with respect to the control group (G1) as the MFGM+2'FL supplemented diet group changed plasma levels. As shown in FIGS. 6A and 6B, the piglet group with supplemented MFGM+2'FL (G5) had significantly more arachidonoyl-GPCs in the plasma on day 14 compared to the control group (G1) but not to the MFGM fed group. For example, the day 14 plasma concentration levels of FIG. 6A show the surprisingly higher plasma concentrations of phosphatidylcholines with ARA—1-linoleoyl-2-arachidonoyl-GPC (18:2/20:4n6) and the day 14 plasma concentration levels of FIG. 6B show the surprisingly higher plasma concentrations of phosphatidylcholines with ARA—1-stearoyl-2-arachidonoyl-GPC (18:0/20:4) when MFGM and 2'FL are administered with long chain polyunsaturated fatty acids (LCPUFAs) such as AA or ARA.

Figure 7A:
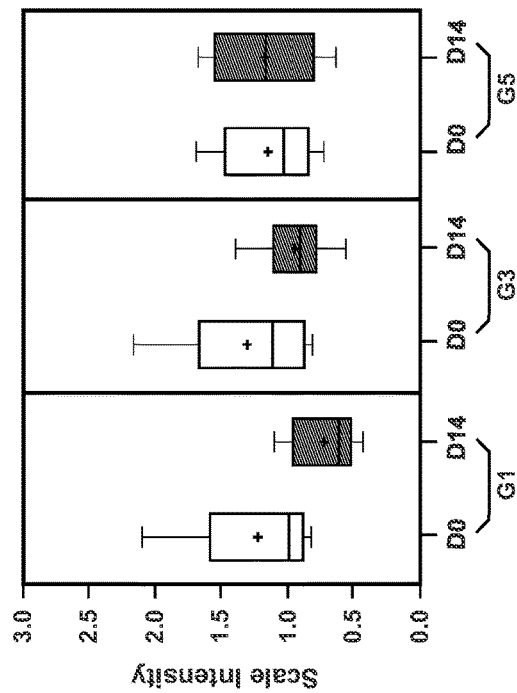
FIGS. 7A and 7B are box charts showing the plasma levels of phosphatidylcholines over time on day 0 and day 14 in piglets given: a control diet, the first column; a diet containing MFGM, the second column; and a formula/composition containing both the MFGM and 2'FL, the third column.
Figure 7B:
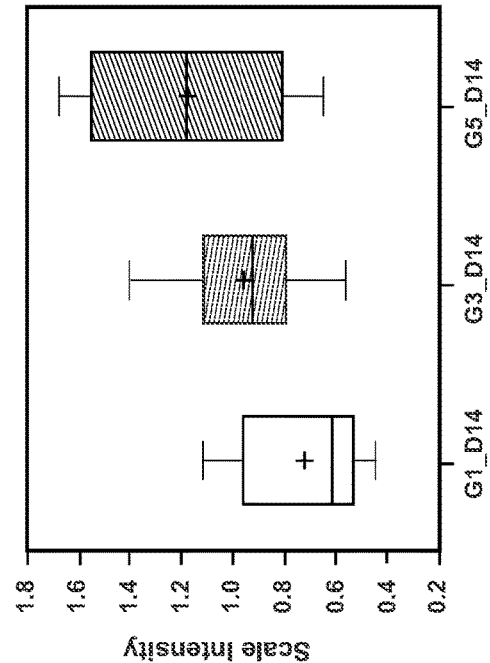

Referring to FIGS. 7A and 7B, the plasma levels of 1-stearoyl-2-docosahexaenoyl-GPC (18:0/22:6) (see FIG. 7A) and 1-palmitoyl-2-docosahexaenoyl-GPC (16:0/22:6) (see FIG. 7B) are illustrated in piglets fed the control (G1), MFGM supplemented (G3), or MFGM and 2'FL supplemented (G5) diets on day 0 and day 14. The same trend of decreasing phosphatidylcholine containing fatty acid docosahexaenoyl (22:6) was observed in the piglet groups fed with the control diet and the MFGM diet. As shown in FIGS. 7A and 7B, the plasma levels of 1-stearoyl-2-docosahexaenoyl-GPC (18:0/22:6) and 1-palmitoyl-2-docosahexaenoyl-GPC (16:0/22:6) decreased over time in the control group and MFGM-fed piglet group (G1 and G3), from day 0 to day 14. In contrast, a significant increase over time was observed for 1-stearoyl-2-docosa hexaenoyl-GPC (18:0/22:6) and 1-palmitoyl-2-docosahexaenoyl-GPC (16:0/22:6) in the MFGM+2'FL group (G5). FIGS. 7A and 7B illustrate the unexpected and surprisingly higher plasma levels of phosphatidylcholine containing the fatty acid docosahexaenoic acid (DHA), namely 1-palmitoyl-2-docosahexaenoyl-GPC (16:0/22:6) in piglets who were fed nutritional compositions/infant formulas containing both MFGM and 2'FL.

Figure 7C:
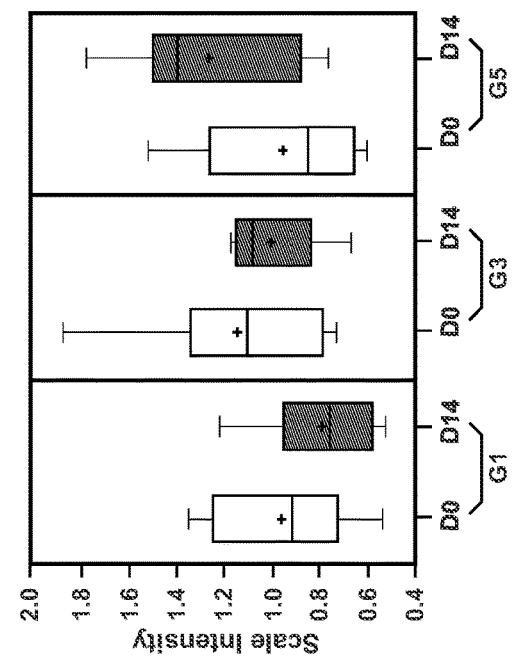
FIG. 7C is a box chart showing the 14 day plasma levels of phosphatidylcholines provided in FIG. 7A.
Figure 7D:
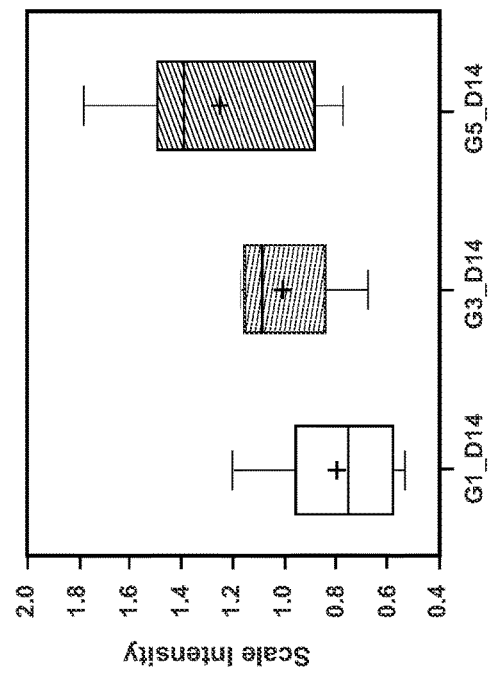
FIG. 7D is a box chart showing the 14 day plasma levels of phosphatidylcholines provided in FIG. 7B.

Referring now to FIGS. 7C and 7D, the 1-stearoyl-2-docosahexaenoyl-GPC (18:0/22:6) and 1-palmitoyl-2-docosahexaenoyl-GPC (16:0/22:6) plasma levels on day 14, respectively, were noted to be significantly higher in the MFGM+2'FL group as compared to the control but not the MFGM-fed group. The 1-palmitoyl-2-docosahexaenoyl-GPC (16:0/22:6) levels decreased significantly in the control group (see FIG. 7B) while not as pronounced in the MFGM supplemented groups. Still referring to FIGS. 7C and 7D, after 14 days of feeding, the 1-stearoyl-2-docosahexaenoyl-GPC (18:0/22:6) and 1-palmitoyl-2-docosahexaenoyl-GPC (16:0/22:6) plasma levels of these phosphatidylcholines were observed to be significantly higher in the MFGM+2'FL group compared to the control group, but not as pronounced a difference as the MFGM supplemented piglet group.

Nutritional compositions produced, according to the present disclosure, may have phosphatidylcholine in an amount of from about 10 mg to about 300 mg, from about 10 mg to about 200 mg, from about 10 mg to about 100 mg, from about 100 mg to about 300 mg, from about 200 mg to about 300 mg, or from about 50 mg to about 200 mg per reconstituted liter (RL) of nutritional composition. In some aspects, the nutritional composition may include one or more phosphatidylcholine compounds.

Sphingomyelin

Figure 4:
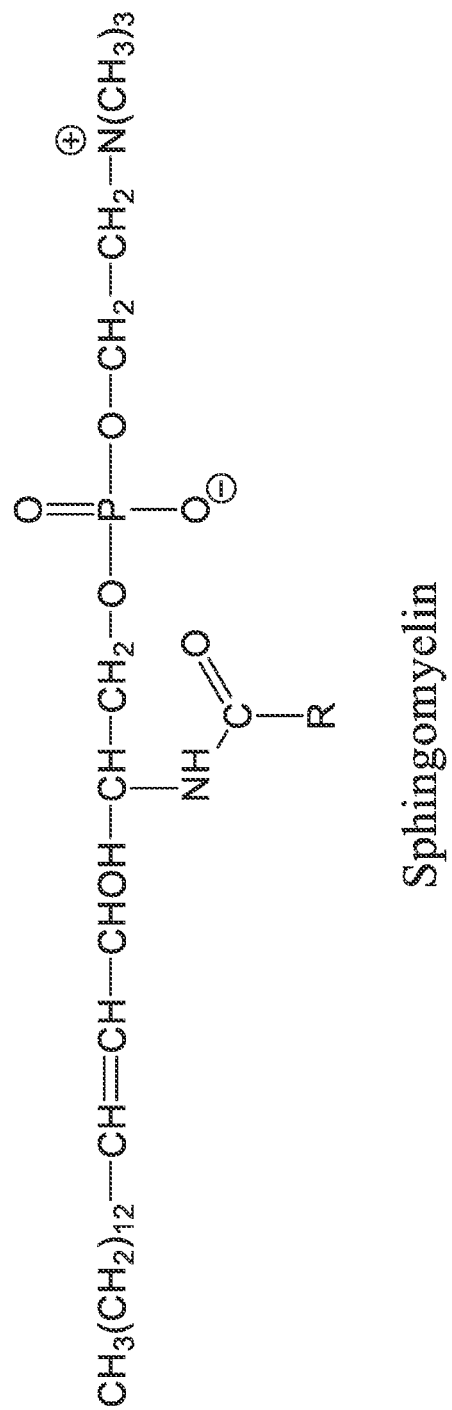
FIG. 4 is the chemical structure of sphingomyelin.

Glycerophospholipids and sphingolipids are quantitatively the most important phospholipids (PLs) in milk. These phospholipids can be located on the milk fat globule membrane (MFGM) and in other membranes in the skim milk. Phosphidolipids include phosphatidylcholine, phosphatidylethanolamine, phosphatidylinositol and phosphatidylserine, while sphingomyelin is the dominant species of sphingolipids. The chemical structure of sphingomyelin is provided in FIG. 4 where R is a fatty acid residue known to those skilled in the art including, for example, Cm, Cm, or other C4 to C28 carbon chains. Sphingolipids are compounds containing a long chain base, the so called sphingoid base (e.g., sphingosine or phytosphingosine), fatty acids and sugars or phosphoric acid or alcohols. Sphingosine is the principal sphingoid base in mammalian sphingolipids, forming a ceramide when its amino group is linked (amide bond), generally, with a saturated fatty acid. Sphingomyelin (SM) is the dominant species and it is composed of a phosphorylcholine head group linked to the ceramide.

Sphingomyelin (SM) is a component of all cell membranes as the most abundant sphingolipid. It is found in lipids of the brain (white and grey matter), in erythrocytes, and in plasma cells. Sphingomyelin can comprise as much as 50% of the lipids in certain tissues. Sphingolipids are a lipid class defined by the presence of a sphingoid backbone linked to a fatty acid and a headgroup. Sphingomyelins (SMs) comprise nearly 36% of the phospholipids in the MFGM.

Figure 8B:
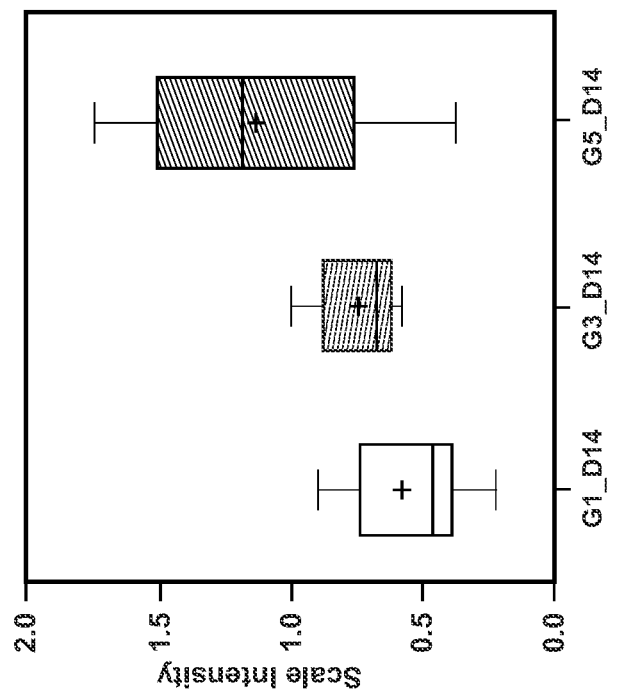
FIG. 8B is a box chart showing plasma levels of sphingomyelin (d18:2/18:1) in group G1 (control), G3 (MFGM) and G5 (MFGM and 2'FL) on day 14 only from the testing shown in FIG. 8A.
Figure 8A:
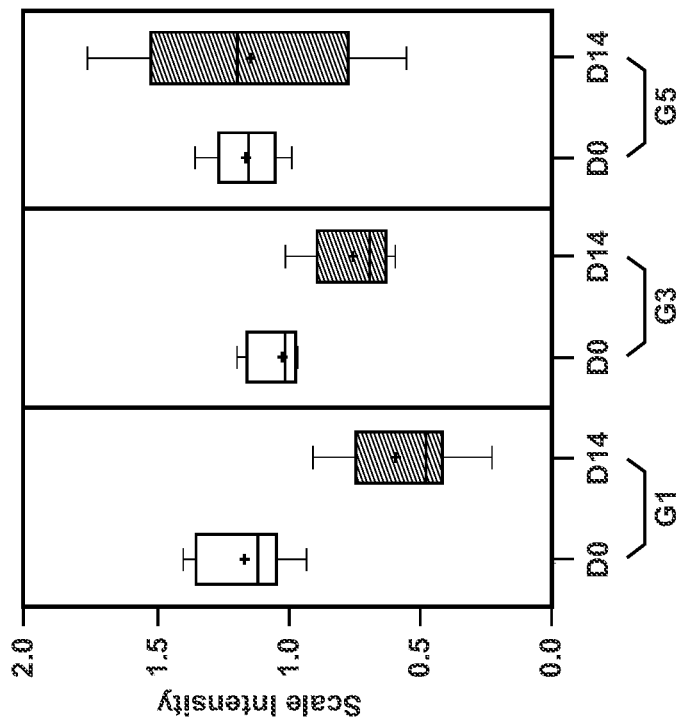
FIG. 8A is a box chart showing plasma levels of sphingomyelin (d18:2/18:1), in group G1 (Control), G3 (MFGM) and G5 (MFGM and 2'FL) on day 0 and day 14 of the testing shown in FIG. 7A.
Figure 9B:
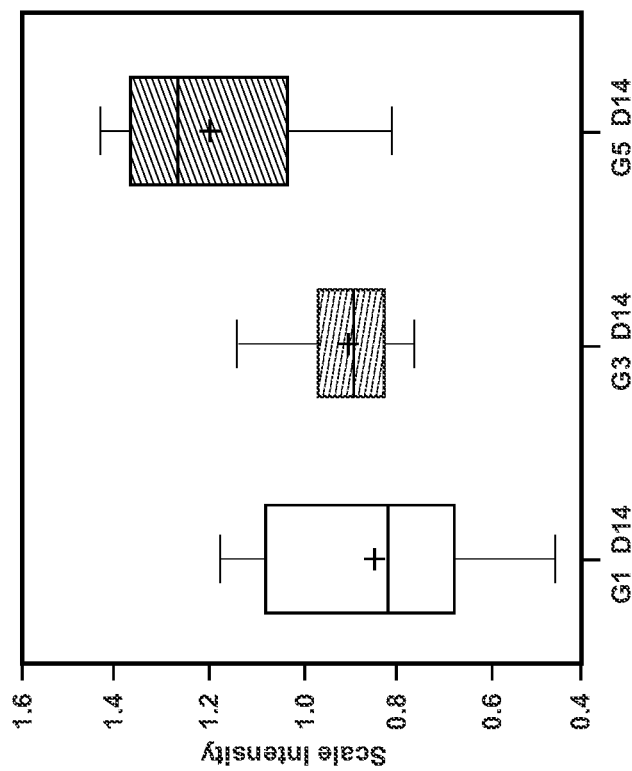
FIG. 9B is a box chart showing plasma levels of tricosanoyl sphingomyelin (d18:1/23:0) plasma levels in group G1 (control), G3 (MFGM) and G5 (MFGM and 2'FL) on day 14.
Figure 9A:
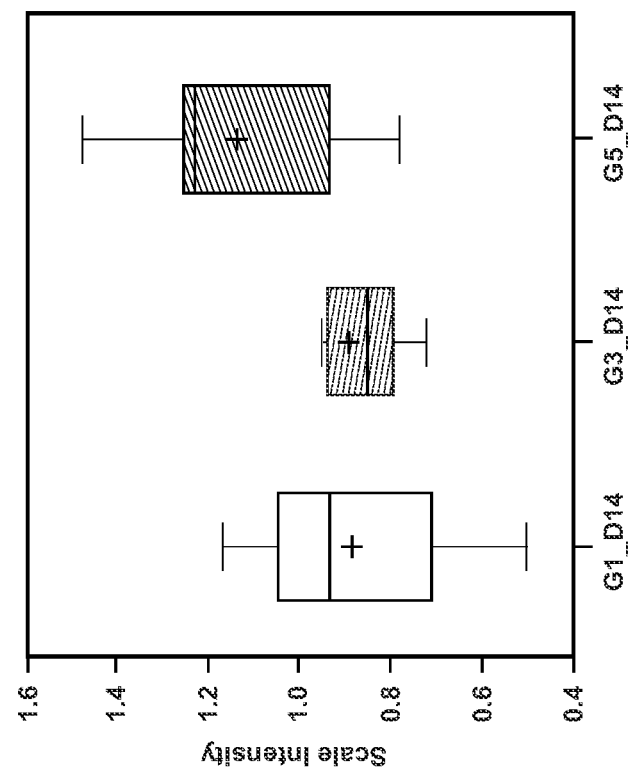
FIG. 9A is a box chart showing plasma levels of behenoyl sphingomyelin (d18:1/22:0) plasma levels in group G1 (control), G3 (MFGM) and G5 (MFGM and 2'FL) on day 14.

Referring to FIG. 8A, the plasma levels of sphingomyelin (d18:2/18:1) are illustrated in piglets fed the control (G1), MFGM supplemented (G3), or MFGM and 2'FL supplemented (G5) diets on day 0 and day 14. FIG. 8A shows the surprisingly better uptake of sphingomyelin in the compositions of the present disclosure incorporating both MFGM and 2'FL. Referring now to FIGS. 8B-9B, at day 14 most of the SM metabolites identified were decreased compared to day 0 in all groups, the control and the supplemented groups. Each of FIGS. 8B, 9A, and 9B shows the surprisingly better uptake of sphingomyelin in the compositions of the present disclosure incorporating both MFGM and 2'FL. This was true for all but three specific SM metabolites, namely behenoyl sphingomyelin (d18:1/22:0); tricosanoyl sphingomyelin (d18:1/23:0); and Sphingomyelin (d18:2/18:1). As shown in FIG. 8A, sphingomyelin (d18:2/18:1) plasma levels decreased in the control group (G1) and in the MFGM supplemented group (G3) from day 0 to day 14, but not in the MFGM+2'FL supplemented group (G5). After 14 days, the change for the sphingomyelin (d18:2/18:1) was significantly higher through the addition of MFGM+2'FL (G5) as compared to MFGM supplemented diet alone (G3).

Referring now to FIGS. 9A and 9B, the plasma levels of behenoyl sphingomyelin (d18:1/22:0) and tricosanoyl sphingomyelin (d18:1/23:0) are illustrated in piglets fed the control (G1), MFGM supplemented (G3), or MFGM and 2'FL supplemented (G5) diets on day 14, which shows the surprisingly better uptake of sphingomyelin in the compositions of the present disclosure incorporating both MFGM and 2'FL. As noted in FIG. 9A, the behenoyl sphingomyelin (d18:1/22:0) plasma level decreased significantly in G1 and G3 but not in G5 after 14 days of feeding. At 14 days the plasma levels were significantly higher in the MFGM+2'FL group compared to the MFGM and control-fed piglet groups. A similar observation was made for tricosanoyl sphingomyelin (d18:1/23:0) plasma levels, as shown in FIG. 9B, where the corresponding plasma levels reached significantly higher SM levels on day 14 with the supplementation of MFGM+2'FL (G5) than the G1 and G3 diets.

From the twenty-seven (27) sphingomyelins metabolites identified, a group of fifteen (15) other sphingomyelins were found to have significantly higher plasma levels in the MFGM+2'FL feeding group as compared to the control fed piglets. There was a trend for the MFGM+2'FL to be higher than the MFGM feeding group, although not significantly different for the SMs. The MFGM group (G3) was significantly higher in nine (9) SM metabolites compared to the control group. The increase in sphingomyelins can likely be attributed to the dietary administration of MFGM, an ingredient rich in sphingolipids. One of the unexpected results identified is the unexpected increase in sphingomyelins due to the 2'FL supplementation, since the 2'FL ingredient does not contain any lipids.

As mentioned above, nutritional compositions of the present disclosure will typically include from about 20 mg to about 400 mg, from about 20 mg to about 300 mg, from about 20 mg to about 200 mg, from about 20 mg to about 100 mg, from about 200 mg to about 400 mg, or from about 100 mg to about 300 mg of sphingomyelin per reconstituted liter (RL) of nutritional composition. In some aspects, the nutritional composition may include one or more sphingomyelin compounds.

Alpha-Tocopherol

Figure 10B:
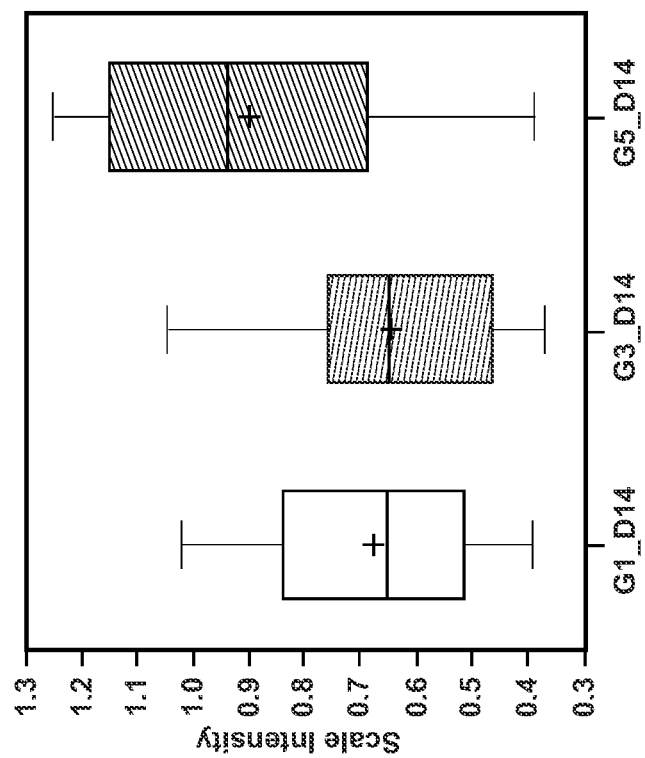
FIG. 10B is a box chart showing plasma levels of alpha-tocopherol on day 14 only in piglets fed the control (G1), MFGM supplemented (G3) and MFGM+2'FL supplemented (G5) diets for the data shown in FIG. 10A.
Figure 10A:
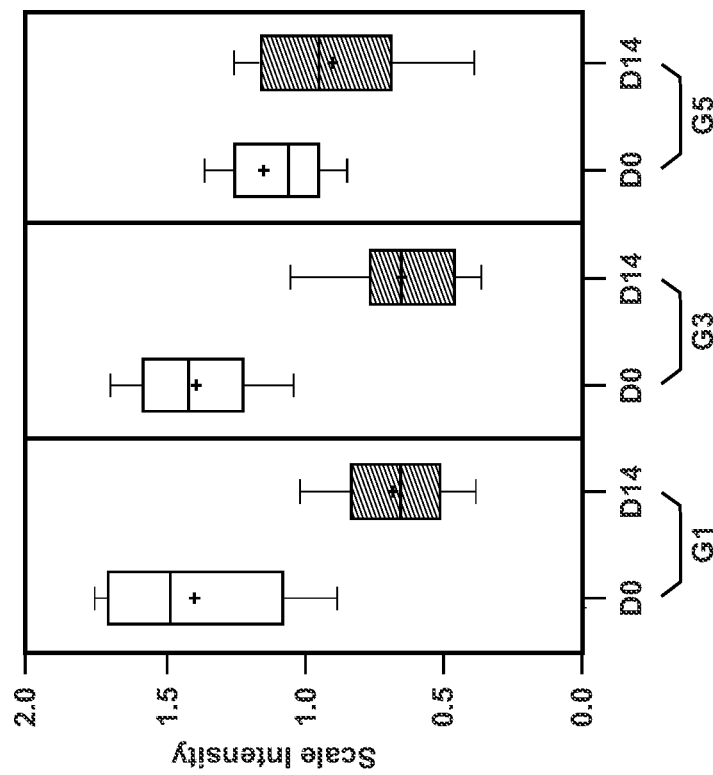
FIG. 10A is a box chart showing plasma levels of alpha-tocopherol on day 0 and day 14 in piglets fed control (G1), MFGM (G3) and MFGM+2'FL diet (G5).

While the compositions of the present disclosure may include any of a variety of vitamins and minerals, the administration of MFGM and 2'FL has a surprising effect on the uptake of vitamin E/alpha-tocopherol as provided in FIGS. 10A and 10B. This effect will be discussed later in the application in more detail. As shown in FIGS. 10A and 10B, the uptake of alpha-tocopherol is surprisingly better in the compositions of the present disclosure incorporating both MFGM and 2'FL, (G5). Vitamin E is a fat-soluble vitamin with anti-oxidant activity. Vitamin E exists in eight chemical forms (alpha-, beta-, gamma- and delta-tocopherol and alpha-, beta-, gamma-, and delta-tocotrienol) that have varying levels of biological activity. Alpha- (or α-) tocopherol is the only form that is recognized to meet human requirements. Alpha tocopherol a tocopherol isomer, the most prevalent form of Vitamin E occurring in the body and the form which can be administered as a supplement.

In some aspects, vitamin E/alpha-tocopherol may be utilized in the nutritional compositions in amounts of from about 1 mg to about 200 mg, from about 1 mg to about 150 mg, from about 1 mg to about 100 mg, from about 1 mg to about 50 mg, from about 5 mg to about 50 mg, from about 10 mg to about 50 mg, from about 10 mg to about 30 mg, from about 20 mg to about 40 mg, from about 30 mg to about 40 mg, from about 15 mg to about 20 mg, or from about 20 mg to about 25 mg per reconstituted liter (RL) of nutritional composition.

Lactoferrin

Lactoferrin (LF) is a bioactive protein present in exocrine fluids such as breast milk, mucosal secretions, secondary granules of neutrophils, and in cerebrospinal fluid (CSF). A variety of bioactive functions have been described for lactoferrin, including anti-oxidative effects. Orally administered LF has been shown to be absorbed into the systemic circulation in infants (with maternal LF). In newborn calves, for example, the oral administration of bovine colostral LF transported the protein into the CSF. The presence of LF receptors have been shown in brain endothelial capillary cells (BCECs) and it is believed that LF enters the BCECs through receptor-mediated endocytosis. Measuring psychological stress in rats through maternal separation demonstrated that milk-derived bLF suppresses distress. Exposing newborn rats to hypoxic conditions results in brain injury. However, feeding LF to rat pups during lactation showed neuroprotective effects on brain metabolism and cerebral gray and white matter recovery. In weaned rats the oral administration of LF improves cognitive performance in stressful tasks. Challenging piglets with a maze task to evaluate spatial learning and memory revealed a better performance for the LF group. As one of the neurotrophic growth factors, Brain-derived neurotrophic factor (BDNF) is expressed in the hippocampus and cortex with important functions in neuronal transmission and contributes to the formation of memory and learning. Piglets receiving the bLF supplementation had significantly increased levels of BDNF in the hippocampus. In addition, using a global gene microarray, the LF diet changes the expression of many pathways involved in neuronal signaling and decreased anxiety.

In some aspects, lactoferrin (LF) may be utilized in nutritional compositions in amounts of from about 0.01 mg to about 150 mg, from about 0.01 mg to about 100 mg, from about 0.01 mg to about 50 mg, from about 0.01 mg to about 25 mg, from about 0.01 mg to about 5 mg, from about 0.01 mg to about 3 mg, from about 0.01 mg to about 1 mg, from about 0.1 mg to about 5 mg, from about 0.1 mg to about 3 mg, or from about 0.1 mg to about 1 mg per reconstituted liter (RL) of nutritional composition.

Nicotinamide

Nicotinamide is the biologically active form of niacin (Vitamin B3). It is a precursor of NAD+ that is used to generate ATP in the mitochondrial electron transport chain. In the brain, nicotinamide has other functional roles such as enhancement of brain choline concentrations from phospholipids or reducing choline clearance from the CSF and prevention of neuronal and vascular cell injury. These functional roles may be attributed to 1-methylnicotinamide (MNA), the endogenous product of nicotinamide methylation by nicotinamide N-methyltransferase (NNMT). 1-Methylnicotinamide exhibits anti-thrombotic and anti-inflammatory actions.

Figure 11B:
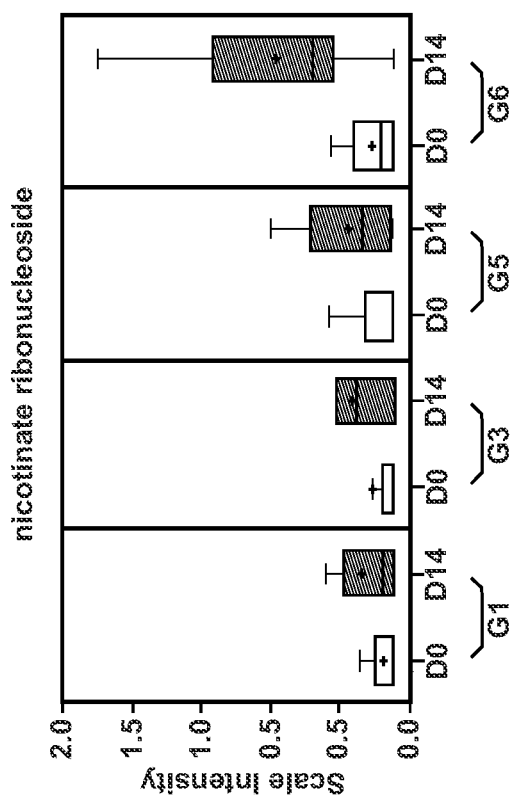
FIGS. 11A and 11B are box charts showing nicotinamide plasma metabolites, nicotinamide (11A) and nicotinate ribonucleoside (11B) in piglets on day 0 and day 14 consuming the G1 (control), G3 (MFGM supplemented), G5 (MFGM+2'FL supplemented), and G6 (MFGM+2'FL+LF supplemented) diets.
Figure 11A:
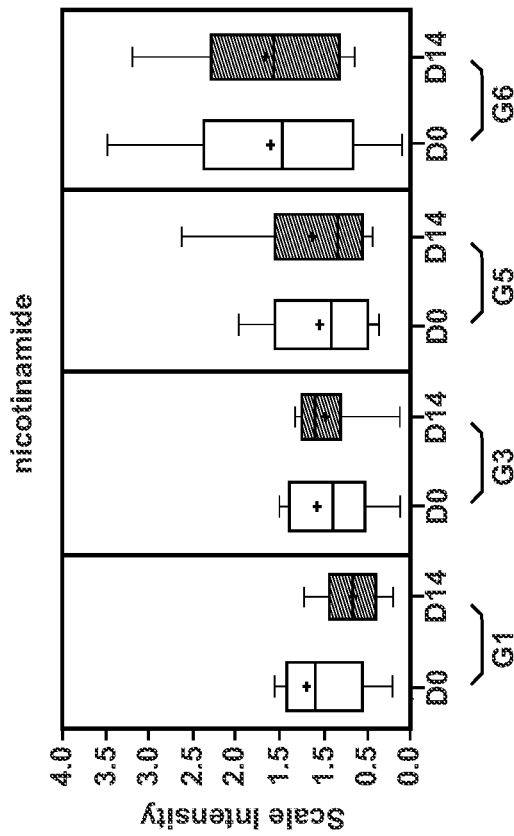

Referring to FIGS. 11A and 11B, nicotinamide plasma metabolites in piglets on day 0 and day 14 are provided for G1 (control group), G3 (MFGM group), G5 (MFGM+2'FL group), and G6 (MFGM+2'FL+LF group). As illustrated in these figures, compared to day 0, the amount of nicotinamide metabolites were either unchanged or significantly lower at Day 14. This effect is presently believed to be the result of alterations in precursor metabolite turnover to support nicotinamide and NAD+ synthesis. In contrast, feeding with diet G6 resulted in significantly higher levels of nicotinate ribonucleoside, nicotinamide, and 1-methlynicotinamide as compared to sow's milk replacer. These changes were not observed in piglets fed the G3 or G5 diets. Thus, the data supports the hypothesis that supplementation with LF in addition to MFGM and 2'FL alters nicotinamide and NAD+ metabolism. Importantly, nicotinamide is not merely a precursor of NAD+. Nicotinamide is an emerging cytoprotectant for both acute and chronic neurodegenerative disorders. In the brain, nicotinamide has functional roles such as prevention of neuronal and vascular cell injury, enhancement of brain choline concentrations, and inhibition of pro-inflammatory cytokines. 1-methylnicotinamide also exhibits anti-thrombotic and anti-inflammatory actions. Thus, elevated levels of these biochemicals may potentially contribute to reduced inflammation in piglets fed diet G6.

Nicotinamide has been used in high doses as therapeutic application in diseases like viral and microbial infections, inflammatory diseases, cerebral ischemia, and diabetes mellitus. It also protects neurons and vascular cells from ischemic reperfusion and other oxidative stresses. In a clinical trial the effect of nicotinamide riboside (NF) was determined regarding elucidating the effect on mitochondrial dysfunction, suggesting that NR may have a potential as therapeutic in diseases that are affected by cellular oxidative stress. Many of these benefits have also been described for lactoferrin. It can be hypothesized that dietary lactoferrin in the piglet diet increased metabolites that support antioxidative effects with long term health benefits. Besides a pediatric application, a recent in vivo study points out the importance of nicotinamides in the postpartum phase. Supplementation with nicotinamide riboside in rodents relieved postpartum metabolic stress, increased lactation, improved nursing behavior and increased BDNF in milk. This led to improved physical and neurobehavioral development of the offspring and benefits persist into adulthood.

Referring to FIG. 11B, the nicotinate ribonucleoside metabolite was significantly higher in G6 than in G1 and G3. There was a trend for G6 being also higher than G5, but the data was not significant. Nicotinamide was significantly higher in G6 compared to the control group G1, but not different than the MFGM supplemented groups G3 and G5 with 2'FL. The metabolite 1-methylnicotinamide was significantly higher in G6 compared to G1 and G5, but not G3. In some aspects, 2'FL seems to downregulate this nicotinate ribonucleoside metabolite.

Figure 12B:
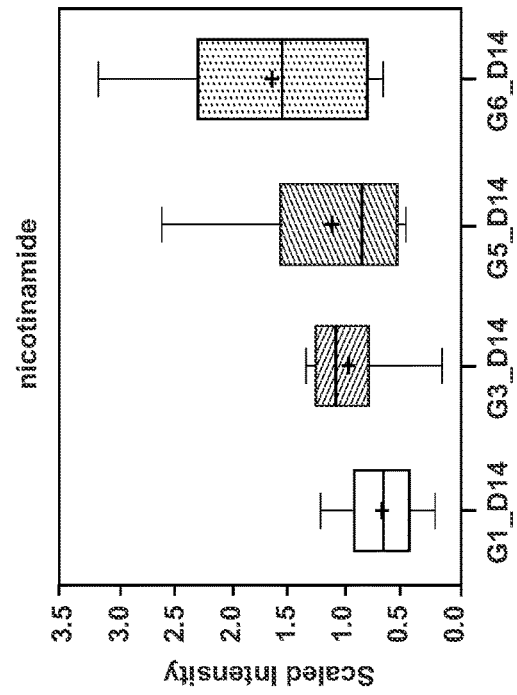
FIGS. 12A, 12B, and 12C are box chart showing nicotinamide plasma metabolites (nicotinate ribonucleoside—FIG. 12A, nicotinamide—FIG. 12B, and 1-methylnicotinamide—FIG. 12C) in piglets on day 14 consuming the G1 (control), G3 (MFGM supplemented), G5 (MFGM+2'FL supplemented), and G6 (MFGM+2'FL+LF supplemented) diets.
Figure 12A:
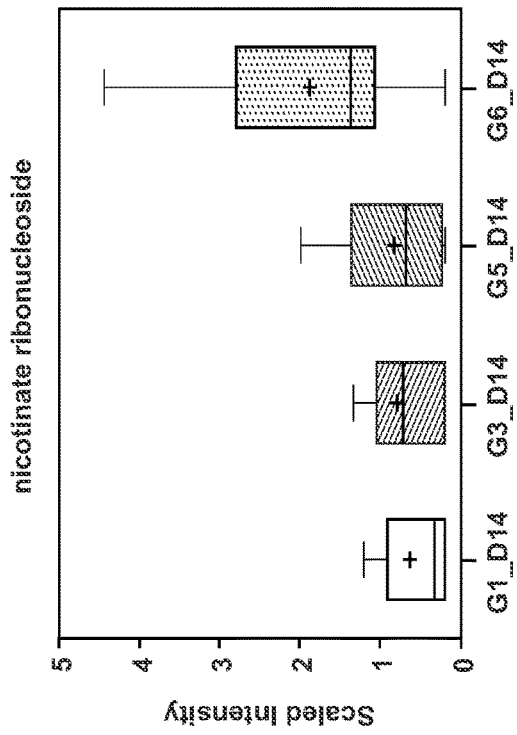
Figure 12C:
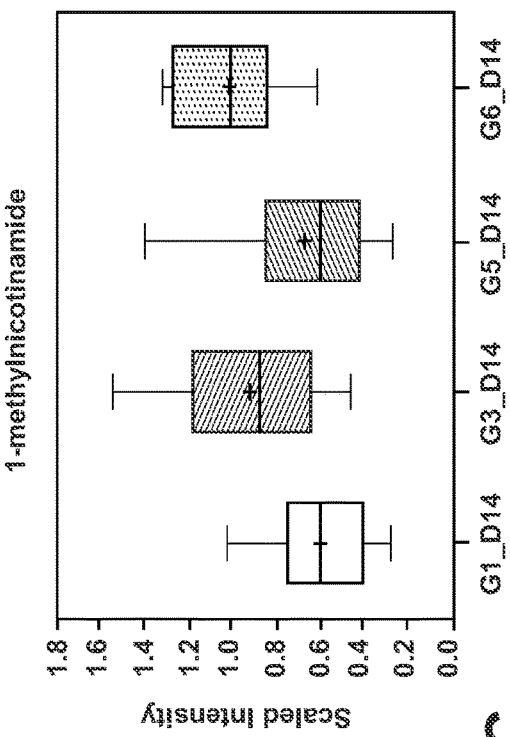

Referring now to FIGS. 12A, 12B, and 12C, plasma levels of nicotinate ribonucleoside, nicotinamide, and 1-methylnicotinamide metabolites are provided after 14 days for piglets fed either the G1 control group, G3 MFGM group, G5 MFGM+2'FL group, or G6 MFGM+2'FL+LF group. Taken together, these data support specific effects of LF on nicotinamide metabolism that could exert profound changes on brain development and inflammation. These novel findings could be applied to the pediatric nutrition in infant formula compositions and human milk fortifiers, as well as maternal nutrition and adult nutrition compositions to address diseases that are associated with metabolic stress including, but not limited to, mitochondrial dysfunction.

In some aspects, the increased uptake of nicotinamide, including corresponding nicotinamide metabolites, in infants or pediatric populations as disclosed herein may improve cellular antioxidant capacity, especially for preterm infants experiencing oxidative stress due to inflammation and bacterial challenge, protecting the brain from oxidative stress. In other aspects, the increased uptake of nicotinamide, including corresponding nicotinamide metabolites, in lactating mothers as disclosed herein can reduce metabolic stress (e.g., hormonal disruption, sleep deprivation), increase lactation, improve nursing behavior, or increase important nutrients in milk. In still other aspects, the increased uptake of nicotinamide, including corresponding nicotinamide metabolites, in adults as disclosed herein can protect against: neurodegenerative disorders (e.g., cognitive decline); anti-inflammatory effects (e.g., viral and bacterial infections, cerebral ischemia, and diabetes mellitus); or anti-thrombotic effects (e.g., blood flow support).

In some aspects, niacin (nicotinic acid) or niacinamide may be utilized in nutritional compositions in amounts of at least 10000 mcg, of at least 10050 mcg, or of at least 10100 mcg per reconstituted liter (RL) of nutritional composition.

Vitamin C

Figure 13:
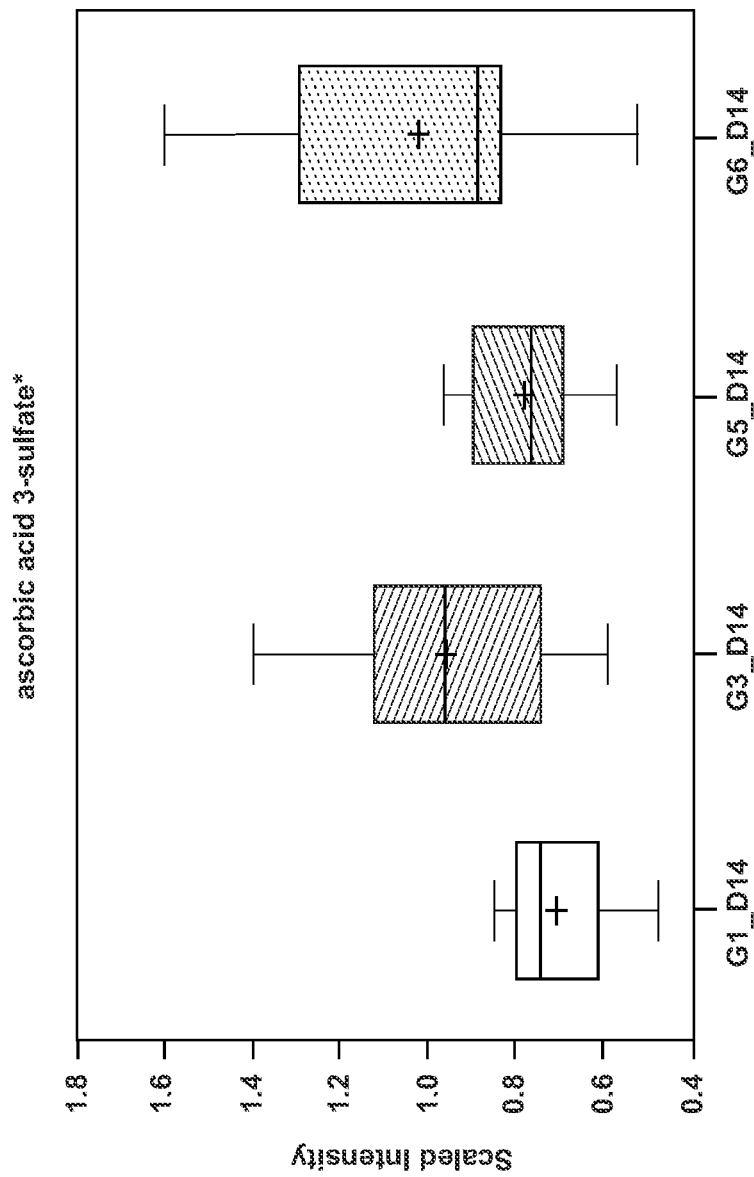
FIG. 13 is a box chart showing vitamin C plasma metabolite (ascorbic acid 3-sulfate) on day 14 in group G1 (control group), G3 (MFGM group), G5 (MFGM+2'FL group), and G6 (MFGM+2'FL+LF group).

Vitamin C (a group of ascorbic acid/ascorbate analogs) is involved in the maintenance of a number of physiological functions. One set of functions is related to the development of the nervous system, including neuronal structure, differentiation, and survival. Additionally, Vitamin C metabolism supports the synthesis of catecholamines and thus the modulation of neurotransmission. In addition, Vitamin C metabolism supports glutathione regeneration and thus plays a critical role in mediating oxidative stress. It has been surprisingly discovered that ascorbate metabolites were significantly lower at day 14 than at day 0 when nutrient compositions of the present disclosure were tested. Following feeding with diet containing MFGM, 2'FL, and LF, ascorbate metabolites were significantly higher than sow's milk replacer. Ascorbate metabolism was unchanged in the control diet and the diet containing MFG and 2'FL, but surprisingly higher in the diets containing just MFGM (without 2'FL—G3) and also in the diet containing MFGM, 2'FL and LF—the G6-fed piglets. These changes suggest that LF exerts a specific effect on ascorbate metabolism. One explanation for this is that LF is an iron transporter in the transferrin family and that ascorbate metabolism is required for intestinal iron absorption. Alternatively or additionally, it is believed LF alters cellular reactive oxygen species and ascorbate metabolism is altered in response. Moreover, ascorbate metabolism is involved in neuronal differentiation and catecholamine biosynthesis. It is additionally believed that LF stimulates these developmental activities and that ascorbate is consumed in the process. Because the ascorbate metabolites are breakdown products, it is believed that LF supplemented animals are catabolizing ascorbate at a higher rate than control animals. In nutritional compositions containing MFGM, 2'FL and LF, the addition of ascorbate may help maximize the benefits of LF supplementation. Furthermore, the metabolite changes induced by LF are consistent with a role for LF in mediating neonatal brain development. FIG. 13 shows the ascorbic acid 3-sulfate plasma metabolite on day 14 in groups of piglets fed control group (G1), MFGM (G3), MFGM and 2'FL (G5) and MFGM, 2'FL and LF (G6).

In some aspects, the increased uptake of vitamin C in infants or pediatric populations as disclosed herein may: improve cellular antioxidant capacity, especially for preterm infants experiencing oxidative stress due to inflammation and bacterial challenge; protecting the brain from oxidative stress; promote healthy growth through protecting DNA; support iron uptake; and assist in neuronal differentiation. In other aspects, the increased uptake of vitamin C in lactating mothers as disclosed herein can: reduce metabolic stress; increase lactation; improve nursing behavior; increase important nutrients in milk; and in smoking mothers, improve the respiratory function in the infant. In still other aspects, the increased uptake of vitamin C in adults as disclosed herein can protect against cataracts; improve deficiency related to age-related cognitive decline and in stroke; support skin and heart health; and promote immune modulation during infection.

In some aspects, Vitamin C (ascorbic acid) may be utilized in nutritional compositions in amounts of from about 10 mg to about 500 mg, from about 10 mg to about 250 mg, from about 10 mg to about 200 mg, from about 10 mg to about 100 mg, from about 50 mg to about 250 mg, from about 50 mg to about 200 mg, from about 50 mg to about 100 mg, from about 100 mg to about 250 mg, from about 100 mg to about 200 mg, from about 150 mg to about 250 mg, from about 150 mg to about 200 mg, or from about 150 mg to about 175 mg per reconstituted liter (RL) of nutritional composition.

Plasma Threonate

Threonic acid can be derived from glycated proteins or from degradation of ascorbic acid. It is a normal component of aqueous humour and blood. Threonic acid is a substrate of L-threonate 3-dehydrogenase in ascorbate and aldarate metabolism pathway. It has also been found to be a microbial metabolite. Since the piglet group that received the MFGM+2'FL+LF diet had increased ascorbic acid levels, it is more likely that the increased threonate levels are degradation products of ascorbic acid. A possible protective effect of lactoferrin as antioxidant on ascorbic acid, consequently higher threonate levels could have significant health implications, in particular to brain development and maintenance of cognitive functions.

The dietary source of threonate, the magnesium-L-threonate has shown to improve learning, working memory, and short-term memory and long-term memory in rats. An increase in brain magnesium was suggested to enhance both short-term synaptic facilitation and long-term potentiation and improves learning and memory functions.

Figure 14:
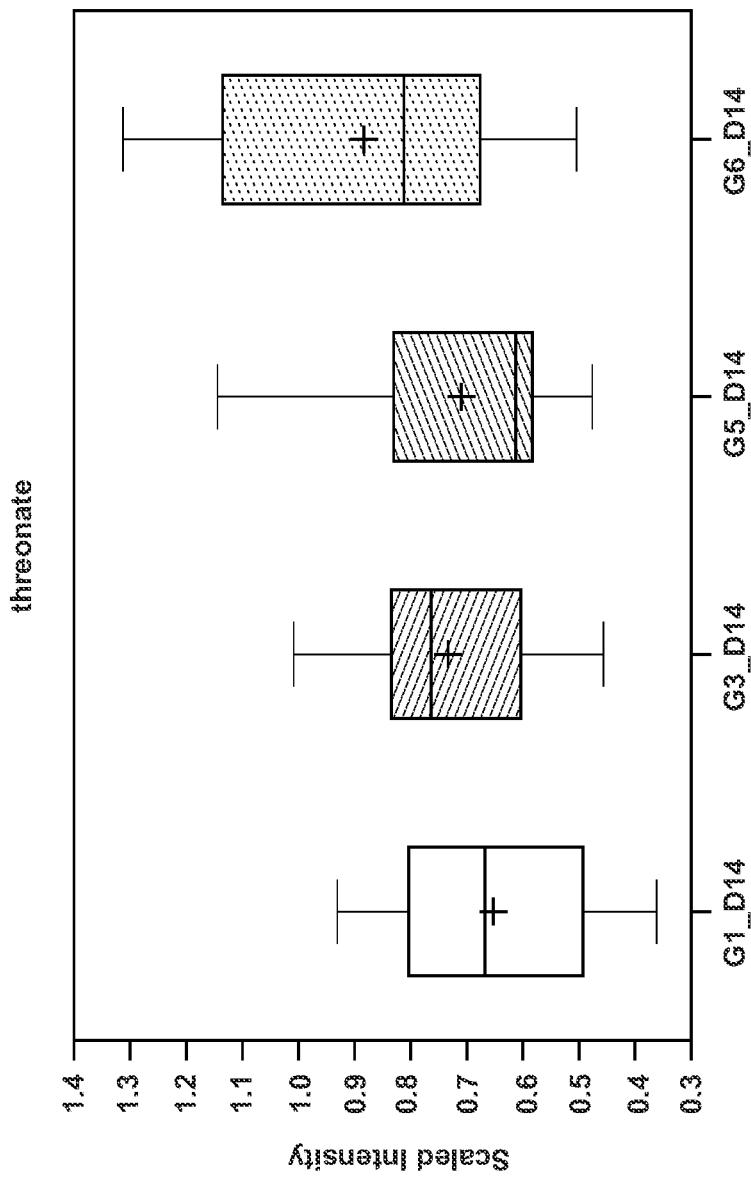
FIG. 14 is a box chart showing plasma metabolite (threonate) on day 14 G1 (control group), G3 (MFGM group), G5 (MFGM+2'FL group), and G6 (MFGM+2'FL+LF group).

With threonate as a critical regulator of synaptic plasticity, this novel finding points out the importance of providing a nutritional formulation with lactoferrin to the growing infant where brain development is an ongoing process beyond birth. The supportive effect on cognitive brain functions could be also of importance for an aging brain, respectively reducing or delaying dementia symptoms like Alzheimer disease. Referring to FIG. 14, a box chart is provided illustrating the day 14 plasma concentration of plasma threonate metabolite in piglets fed a nutritional composition, such as an artificially produced infant formula, including a control group diet (G1), a MFGM supplemented diet (G3), a MFGM and 2'FL supplemented diet (G5) and a MFGM, 2'FL and LF (G6) supplemented diet. The group fed the LF, MFGM, and 2'FL supplemented diet shows a surprising and unexpected increase in threonate as compared to the control, the MFGM supplemented alone, or the combination of MFGM and 2'FL supplemented diets.

Additional Optional Ingredients

It will be understood by one having ordinary skill in the art that construction of the described invention and other components is not limited to any specific material. Other exemplary embodiments of the invention disclosed herein may be formed from a wide variety of materials, unless described otherwise herein. The nutritional compositions, including infant formulas, of the present disclosure may further comprise optional components that may modify the physical, chemical, aesthetic or processing characteristics of the formulas or serve as pharmaceutical or additional nutritional components when used in a targeted population. Non-limiting examples of such optional ingredients include preservatives, anti-oxidants, emulsifying agents, buffers, colorants, flavors, nucleotides, and nucleosides, probiotics, prebiotics such as fructo-oligosaccharides (FOS) and galacto-oligosaccharides (GOS) or mixtures thereof, and related derivatives, thickening agents and stabilizers, and other infant formula or nutritional compositions that will be appreciated in the art of nutritional composition formulation.

The nutritional compositions of the present disclosure may optionally additionally include one or more carotenoids. The carotenoids are believed to provide additional oxidative protection, as well as to further enhance brain development of an infant, child or adult. In exemplary embodiments, the nutritional compositions include lutein, beta-carotene, zeaxanthin, lycopene, and combinations thereof. In one specific embodiment, the nutritional composition includes one or more of lutein and zeaxanthin.

It is generally desirable that the nutritional composition comprises at least one of lutein, lycopene, zeaxanthin, beta-carotene to provide a total amount of carotenoid of from about 0.001 μg/mL to about 5 μg/mL. More particularly, the nutritional compositions may comprise lutein in an amount of from 0.001 μg/mL to 5 μg/mL, including from 0.001 μg/mL to 0.0190 μg/mL, including from 0.001 μg/mL to 0.0140 μg/mL, and also including from 0.044 μg/mL to 5 μg/mL of lutein. In one aspect, the nutritional compositions include a racemic blend of lutein component. In some aspects, the carotenoid in the nutritional composition contains trans-lutein in combination with other lutein forms.

The nutritional compositions may comprise from about 0.001 μg/mL to 5 μg/mL, from 0.001 μg/mL to 0.0130 μg/mL, including from 0.001 μg/mL to 0.0075 μg/mL of lycopene, and also including from 0.0185 μg/L to 5 μg/L of lycopene. The nutritional compositions may comprise from 1 μg/mL to 5 μg/mL, including from 0.001 μg/mL to 0.025 μg/mL of beta-carotene, including from 0.001 to 0.011 μg/mL of beta-carotene, and also including from 0.034 μg/mL to 5 μg/mL of beta-carotene. It should be understood that any combination of these amounts of beta-carotene, lutein, zeaxanthin, and lycopene can be included in the nutritional compositions of the present disclosure. Other carotenoids may optionally be included in the infant formulas as described herein. Any one or all of the carotenoids included in the nutritional compositions or infant formulas described herein may be from a natural source, or artificially synthesized.

Each of the carotenoids in the selected combinations can be obtained from any known or otherwise suitable material source for use in nutritional compositions including infant formulas. Each can be provided individually, or all together, or in any combination and from any number of sources, including sources such as multivitamin premixes containing other vitamins or minerals in combination with one or more of the carotenoids as described herein. Non-limiting examples of some suitable sources of lutein, lycopene, beta-carotene, or combinations thereof include LYCOVIT® lycopene (available from BASF, Mount Olive, N.J.), LYC-O-MATO® tomato extract in oil, powder, or bead form (available from LycoRed Corp., Orange, N.J.), beta-carotene, lutein, or lycopene (available from DSM Nutritional Products, Parsippany, N.J.), FLORAGLO® lutein (available from Kemin Health, Des Moines, Iowa), XANGOLD® Natural Lutein Esters (available from Cognis, Cincinnati, Ohio), and LUCAROTIN® beta-carotene (available from BASF, Mount Olive, N.J.).

The nutritional compositions of the present disclosure may optionally include one or more Probiotic. "Probiotic" is a microorganism with low or no pathogenicity that exerts at least one beneficial effect on the health of the host. An example of a probiotic is a *Lactobacillus* strain such as *Lactobacillus rhamnosus* GG (LGG) or a *Bifidobacterium* strain such as *Bifidobacterium infantis*. In an embodiment, the probiotic(s) may be viable or non-viable. As used herein, the term "viable" refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

The nutritional compositions of the present disclosure may also optionally contain one or a plurality of prebiotics. "Prebiotic" means a non-digestible food ingredient that beneficially affects the host by selectively stimulating the growth and/or activity of one or a limited number of beneficial gut bacteria in the digestive tract, selective reduction in gut pathogens, or favorable influence on gut short chain fatty acid profile that can improve the health of the host. The prebiotic or prebiotics that may be employed in conjunction with the nutritional compositions, including the infant formulas of the present disclosure, include indigestible oligosaccharides such as galacto-oligosaccharide (GOS), fructooligosaccharide(FOS), and/or polydextrose and/or other prebiotic(s).

When an infant formula is the nutritional composition produced according to the present disclosure, the formula/composition is prepared in ways typically done for infant formulas in this art. The process typically begins by blending together the protein source, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water filtered using reverse osmosis, may then be mixed in to form a liquid mixture. The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger. The liquid mixture may then be cooled to about 60° C. to about 85° C.; for example by flash cooling. The liquid mixture may then be homogenized; for example in two stages at about 7 MPa to about 40 MPa in the first stage and about 2 MPa to about 14 MPa in the second stage. The homogenized mixture may then be further cooled to add any heat sensitive components; such as vitamins and minerals. The pH and solids content of the homogenized mixture is conveniently standardized at this point. The homogenized mixture is transferred to a suitable drying apparatus such as a spray drier or freeze drier and converted to powder. The powder should have a moisture content of less than about 5% by weight. If it is desired to add probiotic(s), they may be cultured according to any suitable method and prepared for addition to the infant formula by freeze-drying or spray-drying. Bacterial preparations may be added to the powdered infant formula by dry mixing.

An Example of an infant formula nutritional supplement according to an aspect of the present disclosure includes Example 2 below.

EXAMPLES

| Ingredient | Unit | Example 1 (Per RL) | Example 2 (Per RL) |
| --- | --- | --- | --- |
| Protein | g | 2.09 | 14.23 |
| Carbohydrate | g | 10.7 | 72.5 |
| Fructooligosaccharide (FOS) | g | 0.34 | 2.3 |
| 2'-Fucosyllactose | g | 0.03 | 0.23 |
| Fat | g | 5.7 | 38.75 |
| AA | mg | 18 | 123 |
| DHA | mg | 9 | 61.5 |
| Linoleic Acid | mg | 1000 | 6800 |
| Vitamin A | IU | 441 | 2996 |
| Beta Carotene | IU | 57 | 388 |
| Vitamin D | IU | 83 | 566 |
| Vitamin E | IU | 3.3 | 22.4 |
| Vitamin K | mcg | 11.4 | 77.8 |
| Vitamin B1 | mcg | 204 | 1390 |
| Vitamin B2 | mcg | 260 | 1768 |
| Vitamin B6 | mcg | 125 | 852 |
| Vitamin B12 | mcg | 0.9 | 6 |
| Niacin | mcg | 1499 | 10194 |
| Folic Acid | mcg | 27 | 186 |
| Pantothenic Acid | mcg | 929 | 6318 |
| Biotin | mcg | 7.8 | 53 |
| Vitamin C | mg | 24 | 160 |
| Choline | mg | 32 | 216 |
| Inositol | mg | 29 | 194 |
| Calcium | mg | 94 | 638 |
| Phosphorus | mg | 52 | 351 |
| Magnesium | mg | 9.5 | 65 |
| Iron | mg | 2.1 | 15 |
| Zinc | mg | 1.2 | 8.4 |
| Manganese | mcg | 18 | 120 |
| Copper | mcg | 115 | 784 |
| Iodine | mcg | 28 | 189 |
| Sodium | mg | 30 | 205 |
| Potassium | mg | 134 | 910 |
| Chloride | mg | 76 | 517 |
| Selenium | mcg | 4.8 | 33 |

Nutritional compositions of the present disclosure in the form of an infant formula, including the exemplified formulas described above, can be prepared by any of a variety of known or otherwise effective formulation or manufacturing methods. These methods most typically involve the initial formation of an aqueous slurry containing carbohydrates, proteins, lipids, stabilizers or other formulation aids, vitamins, minerals, or combinations thereof. The slurry is emulsified, pasteurized, homogenized, and cooled. Various other solutions, mixtures, or other materials may be added to the resulting emulsion before, during, or after further processing. This emulsion can then be further diluted, heat-treated, and packaged to form a ready-to-feed or concentrated liquid, or it can be heat-treated and subsequently processed and packaged as a reconstitutable powder, e.g., spray dried, dry mixed, agglomerated.

Nutritional compositions of the present disclosure may be also prepared in the form of ready-to-drink compositions such as nutrition shakes, i.e., liquid nutritional compositions having the consistency, flavor and overall desirable sensory characteristics of common every-day milk shakes, are widely-available consumer products. Examples include the ENSURE®, GLUCERNA®, MYOPLEX® and PEDIASURE® line of nutrition shakes available from Abbott Nutrition of Columbus, Ohio, the MUSCLE MILK® line of nutrition shakes available from CytoSport, Inc. of Benicia, California, and the RESOURCE® line of health shakes available from Nestle, S.A. of Vevey, Switzerland. Generally, they contain balanced amounts of macronutrients (proteins, fats and carbohydrates) as well as micronutrients and flavorings, and are made up in the form of oil-in-water emulsions having the consistency of common every-day milk shakes. When nutritional compositions of the present disclosure are formed into ready-to-drink nutrition compositions, they typically include at least MFGM and 2'FL as well as at least one of LF, alpha-tocopherol, Vitamin C (ascorbic acid), and at least one LCPUFA such as DHA and/or AA. The synergistic effects found by the incorporation of 2'FL and MFGM together on the bioavailability and the availability of these components to be accessible to the parts of the body most needing these nutrients are effective at any age of life. As such, in a teenage, young adult, adult and elderly population, the benefits of the nutritional composition may provide significant health benefits. Dietary Supplements for those in these older populations utilizing the components of the nutritional compositions of the present disclosure may be used to slow, lower or prevent cognitive decline, maintaining brain health; preventing brain inflammation/oxidative stress due to at least the greater uptake into the blood and brain due to the unexpectedly higher levels of phosphatidylcholine bound DHA and ARA.

As discussed above, it has been discovered that alpha-tocopherol bio-availability is surprisingly better when the one or more HMO, typically 2'FL, and MFGM are jointly or simultaneously administered along with any source of alpha-tocopherol (synthetic or natural forms). As a result, Vitamin E is more bio-available and therefore may be administered without administering amounts of Vitamin E in greater amounts than typically administered for the subject. Vitamin E with greater bioavailability may better prevent or lessen the risks of morbidity and mortality in preterm infants when administered in infant formulas. Again, the presence of MFGM and 2'FL cause unexpectedly higher amounts of alpha tocopherol without added amounts of alpha tocopherol being administered. This prevents high doses of supplemental α-tocopherol, which may interfere with the Vitamin K-dependent blood clotting cascade and increase the risk of bleeding in individuals taking anticoagulant drugs. A tolerable upper intake level (UL) for α-tocopherol in adults is set at 1,000 mg/day and applies to all possible stereoisomers of α-tocopherol. The increased bioavailability of Vitamin E in nutritional compositions of the present disclosure means nutritional compositions of the present disclosure may be used to improve visual processing, visual acuity, or both by administering compositions, provide antioxidant effects such as anti-cancer and prevention or lessening of the risk of any metabolic disease(s), prevent or reduce the risk of developing metabolic syndrome, provide anti-aging benefits, antioxidative benefits, slow the effects of Alzheimer's Disease, improve cognitive function, prevent, slow or lessen the effects of cardiovascular disease, and decrease platelet aggregation in response to ADP and ARA. Compositions of the present disclosure are also believed to lessen the risks of adverse effects from other drugs. For example, there is an increased risk of bleeding when administering higher amounts of Vitamin E which might be prevented by use of compositions of the present disclosure, which does not increase the dose, but rather the bioavailability of Vitamin-E/alpha-tocopherol(s). Warfarin (4-hydroxycoumarins) is one such drug, for example.

As discussed above, it has been found that uptake of sphingomyelin is surprisingly better when 2'FL and MFGM are jointly administered and without added amounts of the DHA and/or ARA—normal amounts of these components were administered and yet surprising and unexpected increased bioavailability was observed. Increased uptake of sphingomyelin improves myelination in the brain and therefore improves cognitive function and performance. The "insulating" role (wrapping around the nerve fibers) for myelin is essential for normal motor function (i.e. movement such as walking), sensory function (e.g. hearing, seeing or feeling the sensation of pain) and cognition (e.g. acquiring and recalling knowledge), as demonstrated by the consequences of disorders that affect it, such as the genetically determined leukodystrophies; the acquired inflammatory demyelinating disorder, multiple sclerosis; and the inflammatory demyelinating peripheral neuropathies. Due to its high prevalence, multiple sclerosis, which specifically affects the central nervous system (brain, spinal cord and optic nerve), is the best known disorder of myelin. Myelin increases the speed by which the nerves can communicate with one another. Accordingly, it is believed that nutritional compositions of the present disclosure may be used to lower the risk of, slow the progression of or otherwise affect the above conditions and improve the functioning of nerve fibers and/or brain function.

Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. It will be understood that any described processes or steps within described processes may be combined with other disclosed processes or steps to form compositions within the scope of the present invention. The exemplary compositions and processes disclosed herein are for illustrative purposes and are not to be construed as limiting.

The nutritional compositions of the present disclosure may be used to support weight loss, reduce blood lipid levels, reduce systemic inflammation, reduce inflammation of white adipose tissue, decrease cardiovascular morbidity, and the incidence of type 2 diabetes in humans.

The nutritional compositions of the present disclosure may be used to increase the presence of arachidonic and docosahexaenoic phosphatidylcholines in the plasma of diabetic pregnant women and provide a maximal supply of PUFAs (e.g. DHA) to the fetus of a pregnant woman.

The nutritional compositions of the present disclosure may be used to increase the presence of arachidonic and docosahexaenoic phosphatidylcholines in the milk of breastfeeding women thereby providing a maximal supply of PUFAs (e.g. DHA) to the breastfed infant.

The nutritional compositions of the present disclosure may be used to provide LCPUFA to the brain in a subject that is deficient for the prevention and treatment of neurological diseases like Alzheimer's Disease, Parkinson, schizophrenia and depression.

The nutritional compositions of the present disclosure may be used to provide increased alpha-tocopherol in plasma, for the treatment of diseases associated with metabolic syndrome like NASH, Type 2 diabetes, and coronary heart diseases.

The nutritional compositions of the present disclosure may be used to provide increased alpha-tocopherol in the blood and thereby reduces inflammation in diseases associated with the metabolic syndrome like obesity. The increase in alpha-tocopherol also improves symptoms of neurodegenerative diseases.

It is also to be understood that variations and modifications can be made on the aforementioned compositions and methods without departing from the concepts of the present invention, and further it is to be understood that such concepts are intended to be covered by the following claims unless these claims by their language expressly state otherwise.

What is claimed is:

1. A method for supporting cognitive function and/or neuron cellular health in an individual in need thereof, comprising the step of administering to the individual a therapeutically effective amount of a nutritional composition,
    wherein the nutritional composition comprises a milk fat globule membrane component, at least one human milk oligosaccharide, and docosahexaenoic acid (DHA),
    wherein the DHA is converted to a phospholipid form of the DHA in the gastrointestinal tract of the individual, and
    wherein the level of the phospholipid form of the DHA in the blood of the individual is increased following said administering as compared to blood of an individual administered an otherwise identical nutritional composition not comprising said at least one human milk oligosaccharide.

2. The method of claim 1, wherein the at least one human milk oligosaccharide comprises 2'-fucosyllactose (2'FL) and the nutritional composition further comprises at least one additional component chosen from the group consisting of arachidonic acid (ARA), Vitamin E, Vitamin C, and sphingomyelin.

3. The method of claim 1, wherein the milk fat globule membrane has a lactose content of not more than about 5% by weight of the milk fat globule membrane component.

4. The method of claim 3, wherein the milk fat globule membrane component has a protein content of at least about 75% by weight of the milk fat globule membrane component.

5. The method of claim 1, wherein the at least one human milk oligosaccharide consists of 2'FL and is free of any dietary butyrate.

6. The method of claim 1, wherein the at least one human milk oligosaccharide comprises at least one human milk oligosaccharide chosen from the group consisting of fucosyllactose, 2'FL, 3FL, Lacto-N-fucopentaose I (LNFP I), LNFP II, LNFP III, LNFP V, and mixtures thereof.

7. The method of claim 6, wherein the at least one human milk oligosaccharide is 2'FL and the milk fat globule membrane component comprises from about 10% to about 25% fat by weight of the milk fat globule component; water present in an amount such that the milk fat globule component has a moisture content of not more than 7% by weight of the milk fat globule component; ash present in an amount of not more than 5% by weight of the milk fat globule component; and one or more phospholipids where the total amount of phospholipids in the milk fat globule component is from about 4% to about 9% by weight of the milk fat globule component.

8. The method of claim 1, wherein the nutritional composition is free of butyrate.

* * * * *